United States Patent [19]
Benedict et al.

[11] Patent Number: 5,843,885
[45] Date of Patent: Dec. 1, 1998

[54] ICAM-1/LFA-1 SHORT-CHAIN PEPTIDES AND METHOD OF USING SAME

[75] Inventors: Stephen Benedict; Teruna J. Siahaan; Marcia A. Chan; Scott A. Tibbetts, all of Lawrence, Kans.

[73] Assignee: The University of Kansas, Lawrence, Kans.

[21] Appl. No.: 789,078

[22] Filed: Feb. 3, 1997

Related U.S. Application Data

[63] Continuation of Ser. No. 229,513, Apr. 19, 1994, abandoned.
[51] Int. Cl.$^6$ .......................... A61K 38/02; C07K 14/00; C07K 7/04
[52] U.S. Cl. .............................. 514/2; 530/350; 530/324; 530/325; 530/326; 530/300; 514/12; 514/13
[58] Field of Search .................................. 514/12, 13, 2; 530/324, 325, 326, 350, 300

[56] References Cited

U.S. PATENT DOCUMENTS 5,340,800   8/1994   Liu et al. ..................................... 514/2

FOREIGN PATENT DOCUMENTS

| | | |
|---|---|---|
| 0362526 | 4/1990 | European Pat. Off. . |
| 0391088 | 8/1990 | European Pat. Off. . |
| 9118010 | 11/1991 | WIPO . |
| 9118011 | 11/1991 | WIPO . |

OTHER PUBLICATIONS

Hyres. Cell 69, 11–25, 1992.
Masumoto, A. and Hemler, M. (5 Jan. 1993) J. Biol. Chem. 268, 228–234.
Li, et al., A Leukocyte Integrin Binding Peptide From Intercellular Adhesion Molecule–2 Stimulates T Cell Adhesion and Natural Killer Cell Activity, The Journal of Biological Chemistry, vol. 268, No. 29, Issue of Oct. 15, pp. 21474–21477, 1993.
The Adhesion Molecule Facts Book, Pigott & Power, Academic Press (San Diego), 1993, pp. 93–97, 74–78.
Landis, et al.; A Novel LFA–1 Activation Epitope Maps to the I Domain, The Journal of Cell Biology, vol. 120. No. 6, Mar. 1993, 1519–1527.
Larson et al.; Primary Structure of The Leukocyte Function–Associated Molecule–1 α Subunit: An Integrin With an Embedded Domain Defining a Protein Superfamily, The Journal of Cell Biology, vol. 108, Feb. 1989, 703–712.
Merrifield, Automated Synthesis of Peptides, Science, vol. 15, 1 Oct. 1965, pp. 178–185.
Ezzell, Antibody Combo Nixes Graft Rejection, Science News, vol. 141, p. 132.
Talento et al., A Single Administration of LFA–1 Antibody Confers Prolonged Allograft Survival, Transplantation, vol. 55, 418–422, No. 2, Feb. 1993.
Nakakura et al., Potent and Effective Prolongation by Anti-–LFA–1 Monoclonal Antibody Monotherapy of Non–Primarily Vascularized Heart Allograft Survival in Mice Without T Cell Depletion, Transplantation, vol. 55, 412–417, No. 2, Feb. 1993.
Nossal, Life, Death and The Immune System, Scientific American, Sep. 1993, pp. 53–62.
Weissman, et al.; How The Immune Systems Develops, Scientific American, Sep/ 1993, pp. 65–72.
Marrack et al.; How The Immune System Recognizes The Body, Scientific American, Sep. 1993, pp. 81–89.
Steinman, Autoimmune Disease, Scientific American, Sep. 1993, pp. 107–114.
Waldman, et al.; The Use of Monoclonal Antibodies to Achieve Immunological Tolerance, Immunology Today, vol. 14, No. 6, 1993.
Tuomanen, Subversion of Leukocyte Adhesion Systems by Respiratory Pathogens, ASM News, vol. 59, No. 6, 1993.
Sherman–Gold, Companies Pursue Therapies Based on Complex Cell Adhesion Molecules, 6–Jul. 1993 Genetic Engineering News.
Springer, Adhesion Receptor of The Immune System; Nature, vol. 346, 2 Aug. 1990.
Isobe, et al. Specific Acceptance of Cardiac Allograft After Treatment with Antibodies to ICAM–1 and LFA–1, Science, vol. 255, Feb. 28, 1992.
Welder, et al.; Inhibition of Cell Adhesion by Microspheres Coated With Recombinant Soluble Intercellular Adhesion Molecule–1, The Journal of Immunology; vol. 150, 2203–2210, No. 6, Mar. 15, 1993.
van Kooyk et al.; Activation of LFA–1 Through A $CA^{2+}$–Dependent Epitope Stimulates Lymphocyte Adhesion, The Journal of Cell Biolgy, vol. 112, No. 2, Jan. 1991, 345–354.
Merrifield, The Chemical Synthesis of Peptides and Proteins, pp. 1–8.
Stanley, et al. Integrin LFA–1 α Subunit Contains an ICAM–1 Binding Site in Domains V and VI; The EMBO Journal, vol. 13, No. 8, pp. 1790–1798, 1994.
Ross, et al.; Inhibition of Molt–4–Endothelial Adherence by Synthetic Peptides From The Sequence of ICAM–1, The Journal of Biological Chemistry, vol. 267, No. 12, Issue of Apr. 25, pp. 8573–8643, 1992.
Randi, et al. I Domain of $α_2$ Integrin Lymphocyte Function–Associated Antigen–1 Contains A Binding Site for Ligand Intercellular Adhesion Molecule–1, The Journal of Biological Chemistry, vol. 269, No. 17, Apr. 29, pp. 12295–12298, 1994.

*Primary Examiner*—Stephen Walsh
*Assistant Examiner*—Nirmal S. Basi
*Attorney, Agent, or Firm*—Hovey, Williams, Timmons & Collins

[57] ABSTRACT

Short-chain peptides replicating fragments of functional domains derived from LFA-1 and ICAM-1 parent protein sequences serve to modulate the ICAM/LFA binding interaction. In one aspect of the invention, this modulation serves to block interprotein binding reactivity, as a peptide of the invention binds to a target protein in a manner that precludes the normal binding reaction between ICAM-1 and LFA-1. In another aspect of the invention, this modulation enhances the reactivity of a first peptide, as a second peptide induces a conformational change in the target protein from a first conformation to a second, more reactive, conformation. The peptides are used according to a method including the steps of providing the proteins and applying them to a population of cells.

19 Claims, 6 Drawing Sheets

ICAM-1/LFA-1 SHORT-CHAIN PEPTIDES AND METHOD OF USING SAME

This application is a continuation, of application Ser. No. 08/229,513, filed Apr. 19, 1994, now abandoned.

SEQUENCE LISTING

A printed Sequence Listing accompanies this application, and has also been submitted with identical contents in the form of a computer-readable ASCII file on a floppy diskette.

BACKGROUND OF THE INVENTION

1. Field of the Invention

The invention pertains to the field of protein chemistry and, more particularly, to short-chain peptides that serve to modulate interprotein interactions. More specifically, these short chain peptides have functional residue sequences that essentially replicate fragments of functional domain sequences in corresponding parent protein molecules, but without replicating the entire parent protein. A first such peptide may be mixed with a second peptide to enhance the functionality of the first peptide by inducing a conformational change in a target protein that is reactive with the first peptide. Similarly, the second peptide may induce a conformational change in the first peptide. Particularly preferred short-chain peptides are taken from parent protein molecule sequences selected from the family of integrins, proteins that react with integrins, and the superfamily of immunoglobulins. The peptides are utilized according to methods including the steps of providing the peptides and applying them to a population of cells.

2. Description of the Prior Art

Certain immune system functions rely upon a critical interprotein binding interaction as a necessary element of immune response. One such binding interaction pertains to a heterophilic interaction between the glycoproteins including Intercellular Adhesion Molecule ("ICAM-1") and Leucocyte Function Associated antigen-1 ("LFA-1"). Examples of published sequences for LFA-1 and ICAM-1 are submitted as Sequence ID No.'s 1, 2, and 3.

It is possible to derive immunological benefits by disrupting the intercellular ICAM/LFA binding interaction through the application of specific monoclonal antibodies ("mAbs"), i.e., anti-ICAM-1 or anti-LFA-1. As reported in Isobe et al., Specific Acceptance of Cardiac Allograft After Treatment With Antibodies to ICAM-1 and LFA-1, 255 SCIENCE 1125–1127 (Feb. 1992), an induced immune tolerance enables the indefinite survival of cardiac allografts between fully incompatible mouse strains subsequent to a six day treatment including the simultaneous application of anti-ICAM-1 and anti-LFA-1 mAbs. Unfortunately, a major problem with the use of mAbs for the purpose of inducing immune-tolerance in a mammal is that these large (e.g., 80–150 kDa) molecules typically also induce an effectiveness-limiting immune response to the mAbs.

LFA-1 has special significance in that it belongs to a family or class of proteins that are known as integrins, and is associated with leukocytes such as T and B cells. The integrin family includes similar glycoproteins that combine two separate protein units as a functional member, i.e., a functional heterodimer formed of a $\beta$ unit and an $\alpha$ unit. These respective units each comprise separate proteins that are anchored within interactive proximity to one another, and can extend outwardly from a cytoplasmic domain, across a transmembrane domain, and beyond the cell membrane. In LFA-1, binding avidity for ICAM-1 involves $Mg^{2+}$ and $Ca^{2+}$ ions that, in part, govern the interaction between the $\beta$ and $\alpha$ units.

The integrin family may be subdivided into two groups wherein common group members share common $\beta$ units. A first group of proteins share the common $\beta1$ (CD29) unit, and typically function by binding to extracellular matrix proteins. This first group includes the VLA-1 (CD49a/CD29), VLA-2 (CD49b/CD29), VLA-3 (CD49c/CD29), VLA-4 (CD49d/CD29), VLA-5 (CD49e/CD29) and VLA-6 (CD49f/CD29) proteins. A second group shares the $\beta2$ unit (CD18), and typically functions in cell to cell interactions. This second group includes LFA-1 (CD18/CD11a), MAC-1 (CD18/CD11b), and p150,95 (CD18/CD11c). The LFA-1$\alpha$ unit (CD11a protein, i.e., Sequence ID No. 2) is the specific heterodimer counterpart to the $\beta2$ unit in LFA-1.

Li et al., A Leukocyte Integrin Binding Peptide from Intercellular Adhesion Molecule-2 Stimulates T Cell Adhesion and Natural Killer Cell Activity, 268 J. Biol. Chem. 21474–21477 (Jul. 20, 1993), report that $\beta2$ integrins, and particularly LFA-1, have a cytoplasmic domain which serves to alter protein configuration via a cellular phosphorylation pathway communicating the integrin and respective cell receptor areas. That is to say, phosphorylation may be activated at a remote receptor site with the result of indirectly inducing conformational changes in the integrin via cytoplasmic phosphorylation.

On the other hand, ICAM-1 proteins are not known to incur phosphorylation induced conformational changes. ICAM-1 is found primarily upon monocytes and endothelial cells, and is widely inducible, or upregulated, on many cells including B and T lymphocytes, thymocytes, dendritic cells, endothelial cells, fibroblasts, keratinocytes, chondrocytes, and epithelial cells. This protein has a co-stimulatory effect upon cytotoxic T-cell interaction, and is utilized in a number of intercellular binding interactions.

Recent developments in the field of protein chemistry confirm that short-chain peptides, which have amino acid residue sequences representing mere fragments of a corresponding parent protein molecule, may exhibit significant levels of biofunctionality. Short-chain peptides that derive from the ICAM-1 protein are known to have utility in blocking binding interactions between cells and viruses. Even so, only a very limited number of specific ICAM-1 based peptides have been shown to be useful.

European Patent Publication No. EP 391,088 A2 indicates that functional derivatives of the intercellular adhesion molecule ("ICAM-1") may be used in anti-viral therapy. These functional derivatives may include functional domains and fragments of the ICAM-1 molecule. The method of using these fragments includes administering them in a manner that prevents viral infection of potential viral host cells by impairing a binding interaction between the cells and rhinoviruses that may contact the cells. The binding interaction to be impaired includes one between an ICAM-1 cellular receptor and a corresponding viral adhesion site. The ICAM-1 fragments impair the cell-to-virus binding interaction by competing with normal cellular ICAM-1 molecules for adhesion to the corresponding viral binding site.

Another publication, PCT/AU91/00205, describes the use of short-chain ICAM-1 based peptides for inhibiting intercellular adhesion in mammals.

SUMMARY OF THE INVENTION

The present invention overcomes the problems outlined above by providing, for methods of use, a variety of short-chain ICAM-1 and LFA-1 based peptides having sufficiently low molecular weights to avoid the induction of a mammalian immune system response of a type that would attack the peptides. These peptides are useful for modulating intercellular binding interactions by blocking or enhancing interprotein reactivity. In some instances, a single peptide can function as both a binding blocker or a binding enhancer, depending upon the peptide concentration. Another aspect of the invention pertains to the use of protein conformation modulator peptides that increase the avidity of these short-chain peptides for binding with naturally occurring ICAM-1 and LFA-1 based target proteins.

Peptides of the invention may have further utility in immunosuppression applications. A specific immune tolerance to organ transplants may be induced by killing T-cells that recognize the transplanted tissues as foreign antigens by mimicking the thymic winnowing of developing T-cells. Cytotoxic T-cells require a two-stage activation, which includes a first signal that results from contacting the T-cell antigen receptor with a specific antigen, and a second signal corresponding to for example the ICAM/LFA binding interaction. In the event that the second signal is blocked, the antigen-activated T-cell is eventually induced to die by apoptosis. Long-term immune tolerance is induced once the population of activatable antigen-specific T-cells dies. In a similar manner, these peptides may be used as an alternative treatment for various diseases where immunosuppression is a common therapy, e.g., Crohn's disease, ulcerative colitis, multiple sclerosis, rheumatoid arthritis, systemic lupus erythematosus, pemphigus vulgaris, pemphigoid, acquired epidermolysis bullous, allergic contact dermatitis, pyoderma gangrenosum, psoriasis, asthma, and diabetes.

Broadly speaking, one facet of the invention pertains to short-chain peptides that serve to promote the efficacy of other short-chain peptides in reacting with target proteins. It has been discovered that, in the case where a first short-chain peptide exhibits a specific type of biofunctionality, a second short-chain modulator peptide can induce conformational changes in a target protein, and these conformational changes can serve to increase the binding of the first protein for the target protein. The second peptide produces this increased level of binding by shifting the target protein from a first conformation to a second, more reactive conformation. Accordingly, a synergism is observed in that the first peptide has an increased level of reactivity with the target protein in the presence of the second peptide. A specific example of the use of modulator peptides includes the LFA-1β based LJCRF-4 (Sequence ID No. 16) peptide, which synergistically increases binding of the LFA-1α based LJCRF-6 (Sequence ID No. 18) peptide for binding with ICAM-1. Alternatively, these modulator peptides may induce a conformational change that decreases reactivity.

Short-chain peptides of the invention, e.g., Sequence ID Nos. 4–18, each preferably replicate a fragment of a functional domain that is based upon or identified from a parent protein molecule. These fragments have a residue sequence length less than the entire parent protein, and exhibit functionality as reactivity with naturally occurring proteins that are the reactive counterparts of the parent protein from which the peptides derive. By way of example, an ICAM-1 based peptide of the invention may consist essentially of the sequence from positions 28–37 of Sequence ID No. 3 (see Table 1). ICAM-1 based peptides compete with naturally occurring ICAM-1 proteins by targeting LFA-1 cellular proteins. Similarly, LFA-1 peptides target ICAM-1 cellular proteins.

These short-chain peptides exhibit biofunctionality as a capacity for modulating the natural ICAM/LFA binding interaction by either acting to block or enhance the level of protein interaction. This modulation results from ICAM-1 or LFA-1 based short-chain peptides that bind to a corresponding natural ICAM-1 or LFA-1 target protein on a cell. By way of example, in this bound position the short-chain peptide can serve to block a T-cell from attaching to another cell by precluding the LFA-1 or ICAM-1 to which the peptide is bound on one cell from interacting in the normal manner with a counterpart binding protein on the other cell.

A preferred form of the invention includes modulating the ICAM/LFA binding interaction by providing short-chain peptides that are based upon functional domain sub-sequences which are taken from the family of integrins. Sub-sequences that are taken from the LFA-1 α and β units are particularly preferred.

Short-chain peptides of the invention preferably have a molecular weight less than about 20 kDa, more preferably less than about 15 kDa, even more preferably less than about 10 kDa, and most preferably less than about 5 kDa, in order to reduce the chance for inducing an undesirable immune response, such as an allergic reaction or the production of antibodies for attacking the peptides, which might otherwise occur after the peptides are injected into a mammal or other organism. Alternatively, peptides of the invention preferably have an amino acid residue sequence of a length less than about 50 residues, more preferably have a length less than about 30 residues, and most preferably have a length less than about 25 residues.

In a study of the ICAM/LFA interaction, the degree of peptide binding to a target protein can be acceptably quantified by using a flow cytometer to measure median fluorescence intensity peak shifts in terms of percentage change from a control peak. In this type of device, a population of cells is individually subjected to a laser fluorescence study for purposes of identifying the presence of fluorescein labeled peptides that previously bound to a target protein on a living cell. The fluorescence intensity results for each cell are plotted in the general shape of a bell curve, and a median intensity peak value is calculated for the test sample as well as a control sample. Median peak shifts greater than about 10% with respect to the control usually indicate a level of functionality beyond that which might be induced by mere laboratory error, and shifts greater than about 20% are particularly good indicators of modulation in the ICAM/LFA binding interaction.

The peptides are used by introducing them into a population of cells. A blocking peptide can be mixed with a modulator peptide for increased in vivo efficacy of the blocking peptide.

Peptides of the invention may be produced by any available method including, by way of example, automated protein synthesis and recombinant host expression.

BRIEF DESCRIPTION OF THE DRAWINGS

FIG. 1 schematically depicts the LFA-1 and ICAM-1 proteins, including special regions of interest such as signal sequences, sequence repeat regions, and suspected functional domains from which short-chain peptides were selected for synthetic replication;

FIG. 2 depicts a Cartesian plot of flow cytometer results that were obtained from one of several fluorescence runs that were conducted to quantify the capacity of the ICAM-1 based SC-3-111 (Sequence ID No. 10) peptide for blocking the specific antibody binding of anti-LFA-1 mAb;

FIG. 3 is a plot similar to FIG. 2, but derived from a sample of the LJCRF-1 (Sequence ID No. 6) peptide;

FIG. 4 depicts a plot of flow cytometer results for the LFA-1 based LJCRF-4 (Sequence ID No. 16) peptide, which functions to promote the specific antibody binding of anti-ICAM-1 mAb;

Figure 8:
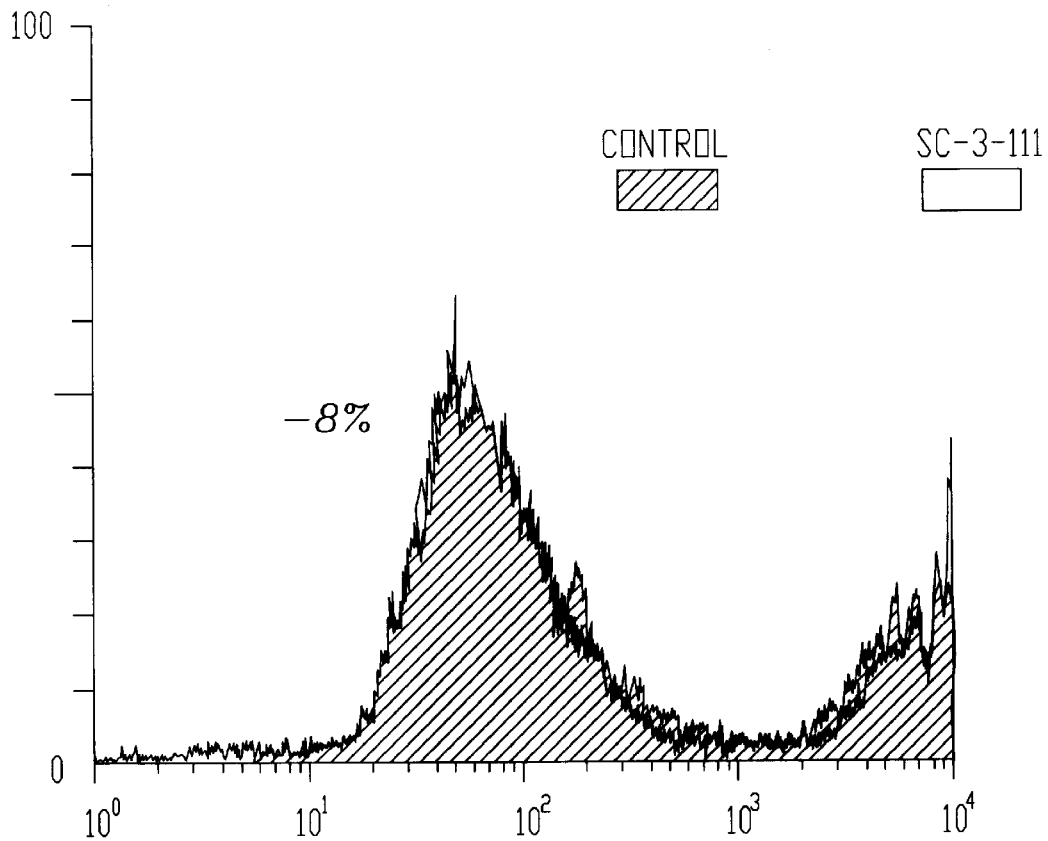
Figure 9:
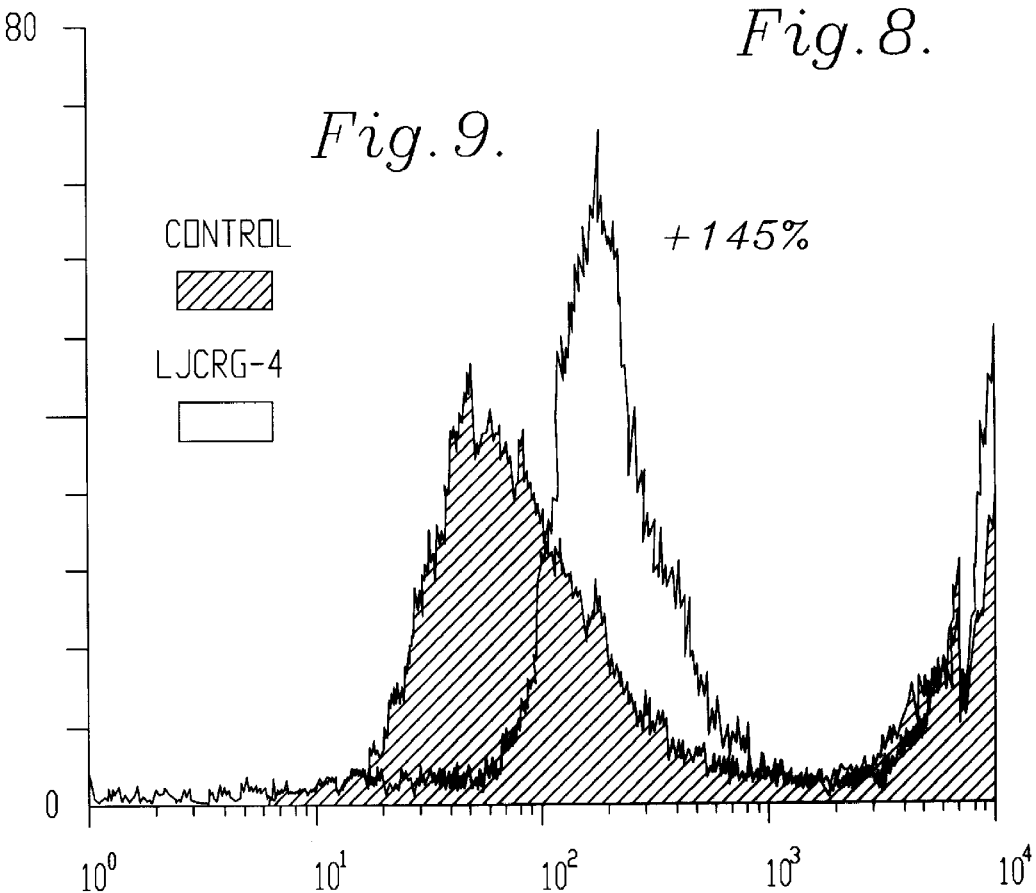

FIG. 8 depicts a plot of flow cytometer results that demonstrate substantially no T-cell binding enhancement of fluorecescein labeled LJCRF-6 (Sequence ID No. 18) peptide in the presence of SC-3-111 (Sequence ID No. 10) peptide; and FIG. 9 depicts a plot of flow cytometer results that demonstrate significant T-cell binding enhancement of fluorecescein labeled LJCRF-6 (Sequence ID No. 18) peptide in the presence of LJCRF-4 (Sequence ID No. 16) peptide.

DETAILED DESCRIPTION OF THE PREFERRED EMBODIMENT

The following examples provide, by way of example, specific methodology that may be utilized to practice preferred forms of the invention.

EXAMPLE 1

Short Chain Polypeptide Identification and Synthesis

Table 1 below identifies synthetically produced amino acid residue sequences replicating functional domain polypeptide fragments from the parent proteins (LFA-1 and ICAM-1) upon which they are based. Parent protein amino acid residue sequences of the integrin LFA-1 include the β or CD18 subunit (Sequence ID NO. 1) and the α or CD11a subunit (Sequence ID NO. 2). The ICAM-1 or CD54 (Sequence ID NO. 3) sequence was used as another parent protein.

These functional domains were selected to include suspected ICAM/LFA interprotein binding sites. The fragments were arbitrarily selected in sub-regions over the domains of interest as short-chain sequences for synthetic replication, with each sequence having no more than about 30 amino acid residues, in order to reduce the molecular weight and reduce the chance of provoking an immune system response in mammals injected with the peptides. These selected sequences are identified as Sequence ID Nos. 4–15 in Table 1. In particular, the synthetic peptides reproduced sub-regions of Sequence ID No. 3 within positions 25–95, and these respective subregions randomly overlapped. Other parent protein regions included positions 130–160 of Sequence ID No. 1, as well as Sequence ID No. 2 positions 260–290 and 465–495.

Table 1 provides a specific positional cross-reference between the synthetic peptide sequences and the parent protein sequences according to the Sequence Listing. Those synthetic peptide sequences having a designation including a "LJCRF" prefix were synthesized on commercial order by La Jolla Cancer Research Foundation of La Jolla, Calif.

using a Model 430A peptide synthesizer (manufactured by ABI of Foster City, Calif.). This entire peptide synthesis was conducted according to standard solid phase protocols employing t-butyloxy-carbamate amino acid chemistry; i.e., standard techniques described in Atherton and Sheppard, *Solid Phase Peptide Synthesis*, which generally follow the protein synthesis techniques as identified in Merrifield, Automated Synthesis of Peptides, 150 Science 178–185 (October 1965). The remaining sequences were synthesized according to the same protocols at the University of Kansas, Department of Pharmaceutical Chemistry, in Lawrence, Kans.

TABLE 1

SHORT CHAIN SYNTHETIC PEPTIDES
AND SEQUENCE LISTING COMPARISON TO NATURAL PROTEINS

| Designation | Sequence ID | Residue Length | Positional Comparison to |
|---|---|---|---|
| ICAM (CD54) Based Peptides | | | Sequence ID NO. 3 |
| TJS-1-149A | 4 | 21 | 28–48 (Cys at position 48 of Sequence ID NO. 3 is Gly at position 21 of Sequence ID NO. 4) |
| SC-1-232 | 5$_a$ | 22 | 28–48 |
| LJCRF-1 (SC-3-146) | 6 | 21 | 28–48 (Cys at position 48 of Sequence ID NO. 3 is Gly at position 21 of Sequence ID NO. 4) |
| SC-3-150 | 7 | 12 | 37–48 (Ile at position 37 of Sequence ID NO. 3 is Cys at position 1 of Sequence ID No. 7) |
| RB-1-51 | 8$_b$ | 12 | 37–48 (Ile at position 37 of Sequence ID NO. 3 is Cys at position 1 of Sequence ID No. 8) |
| MC-1-80 | 9 | 11 | 38–48 (Cys at position 48 of Sequence ID NO. 3 is Gly at position 11 of Sequence ID NO. 9) |
| SC-3-111 | 10 | 10 | 28–37 |
| LJCRF-2 (SC-3-213) | 11 | 25 | 53–77 |
| LJCRF-3 | 12 | 24 | 67–90 |
| LJCRF-7 | 13 | 10 | 33–42 |
| LJCRF-8 | 14$_c$ | 12 | 33–43 |
| RB-1-52 | 15$_{b,c}$ | 12 | 33–43 |
| LFA-1 β (CD18) Based Peptides | | | Sequence ID NO. 1 |
| LJCRF-4 | 16 | 25 | 134–159 (Met at position 139 of Sequence ID NO. 1 was not synthetically reproduced because of the problem with oxidation of Met) |
| LFA-1 α (CD 11a) Based Peptides | | | Sequence ID NO. 2 |
| LJCRF-5 | 17 | 24 | 466–491 (Leu Leu at positions 478 and 479 of Sequence ID No. 2 were not synthetically reproduced because of the problem of synthesizing three Leu in a row) |
| LJCRF-6 | 18 | 24 | 262–286 (Arg at position 281 of Sequence ID NO. 2 was not synthetically reproduced because the first attempt at synthesis had difficulty in replicating this residue) |
| RB-1-88 | 19$_d$ | 24 | 262–286 (Arg at position 281 of |

TABLE 1-continued

SHORT CHAIN SYNTHETIC PEPTIDES
AND SEQUENCE LISTING COMPARISON TO NATURAL PROTEINS

| Designation | Sequence ID | Residue Length | Positional Comparison to |
|---|---|---|---|
| | | | Sequence ID NO. 2 was not synthetically reproduced because the first attempt at synthesis had difficulty in replicating this residue) |

NOTES:
a Xaa is coumarin.
b Cyclic peptide having a disulfide bond between Cys and/or Pen residues formed by dropwise addition of 2% (aqueous) potassium ferricyanide solution to a dilute solution of their respective linear peptides at pH 7.8.
c Xaa is penicillamine.
d Xaa is fluorescein isothiocyanate.

EXAMPLE 2

An Antibody Binding Assay

An antibody binding assay was performed to demonstrate that peptides of the invention can change the ability of anti-LFA-1 and anti-ICAM-1 mAbs to bind with to human T-cells. The T-cells were selected as Molt3 cells, a leukemia-derived human T-cell line that was purchased from American Type Culture Collection of Rockville, Md., and which had a catalog number CRL-1552.

A 1 ml quantity of the Molt3 inoculum was warmed to 37° C. and transferred by pipette into about 25 ml of a growth culture medium including RPMI 1640 lymphocyte growth medium (Fisher Scientific of St. Louis, Mo.) mixed with 10% by volume fetal calf serum, 100 units/ml penicillin, 100 µg/ml streptomycin and 2 mM glutamine. The inoculated culture was incubated for three to four days at 37° C. under a normal atmosphere having about 5% $CO_2$ added thereto. This culture was capable of being maintained indefinitely by siphoning away the top (non-cell containing) layer and adding 50 ml (or more) of growth culture medium at intervals of three to four days.

An aqueous buffer solution including Dulbecco's phosphate buffered saline and bovine serum albumin ("PBS/BSA solution") was prepared for use, and included a mixture of 200 mg $KH_2PO_4$, 1.15 g $Na_2HPO_4$, 100 mg $CaCl_2$, 200 mg KCl, 100 mg $MgCl_2.6H_2O$, 8 g NaCl, with distilled water added to a final 1 liter volume at room temperature, thus, forming a "PBS" solution of pH 7.4 to which was added 0.5% by weight bovine serum albumin.

An aliquot of about 7 ml was removed from the incubated culture medium and subjected to washing with the PBS/BSA solution. The washing procedure was initiated by placing the aliquot in a centrifuge (Model GT422 from Jouan, distributed Piruscio & Assoc. of Manchester, Mo.) at 1400 rpm for 6.5 minutes to separate the cells from the growth medium. The supernatant fluid was decanted, a 5 ml portion of PBS/BSA solution was transferred by pipette into the pellet, and the mixture was again centrifuged as before. The resulting supernatant fluid was decanted and the cells from the pellet were resuspended in PBS/BSA solution at a titer of about $1 \times 10^6$ cells/ml. A 500 µl portion of the solution containing the resuspended cells was placed in a microcentrifuge (Marathon 13K/M from Fisher Scientific of St. Louis, Mo.) at 3500 rpm for six minutes, to provide a washed pellet.

The washed pellet was resuspended in a 25 µl peptide cocktail including PBS solution mixed with 455 nmol of the LJCRF-1 peptide described in Table 1 above. The cells were incubated with the peptide cocktail at 37° C. for 45 minutes.

After incubation with the peptide cocktail, several antibodies were successively mixed into the incubated solution. A 75 µl portion of anti-IgM solution (a mixture of 10 µl of goat anti-human IgM stock purchased from Jackson Immuno Research of Westgrove, Pa; and 65 µl of PBS/BSA solution) was added to the peptide cocktail for blocking of nonspecific binding of the secondary antibody. The resulting mixture was incubated for 10 minutes on ice. About 0.1 µg of a primary antibody including mouse IgG anti-human CD11a (purified according to conventional protocols at the University of Kansas Department of Pharmacology and Toxicology from an American Type Culture hybridoma cell line having Catalogue Number HB-202) was next stirred into the mixture, which was then incubated for 30 minutes at room temperature. The incubated mixture was placed in a microcentrifuge at 3500 rpm for six minutes to remove the cells from the mixture, and the cell pellet was washed two times by adding 500 µl aliquots of PBS/BSA solution and microfuging to remove non-bound antibodies from the cells as before. The resulting washed pellet was resuspended in 100 µl of a secondary antibody cocktail including 5 µl of fluorescein isothiocyanate ("FITC") labeled goat anti-mouse IgG (from CALTAG of South San Francisco, Calif.) and 95 µl of PBS/BSA solution. The resulting solution was incubated for 30 minutes at room temperature in the dark.

The incubated solution including the secondary antibody cocktail was microfuged at 3500 rpm for six minutes to remove the cells from the solution, and the cell pellet was washed two times with 500 µl portions of PBS/BSA solution, as before, to remove unbound antibodies. The washed pellet was resuspended in 500 µl of PBS/BSA solution, and the mixture was assayed in a flow cytometer (FACscan from Becton-Dickinson of San Jose, Calif.) to obtain a fluorescein fluorescence intensity analysis at 520 nm following laser excitation of the individual cells at 488 nm.

Identical peptide assays to that described above were conducted for several of the synthetic peptides listed in Table 1, using respective 455 nmol amounts of each peptide in the corresponding peptide cocktails. In these additional assays, mouse IgG anti-human CD54 (purchased from Cambridge Research Biochemicals of Wilmington, Del.) was substituted for the primary antibody in each instance where the peptide was based on an LFA-1 positional reference.

Figure 1:
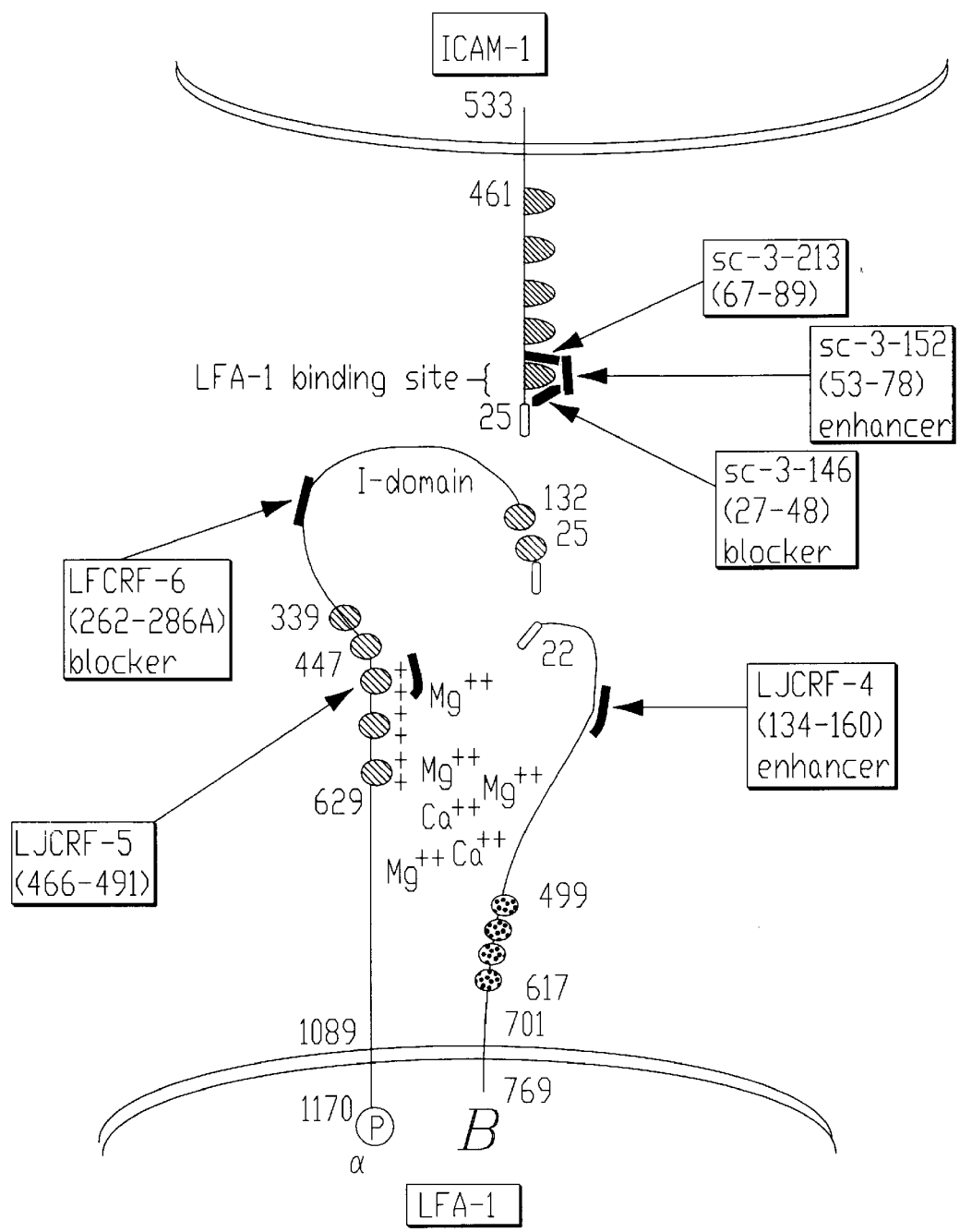
Figure 2:
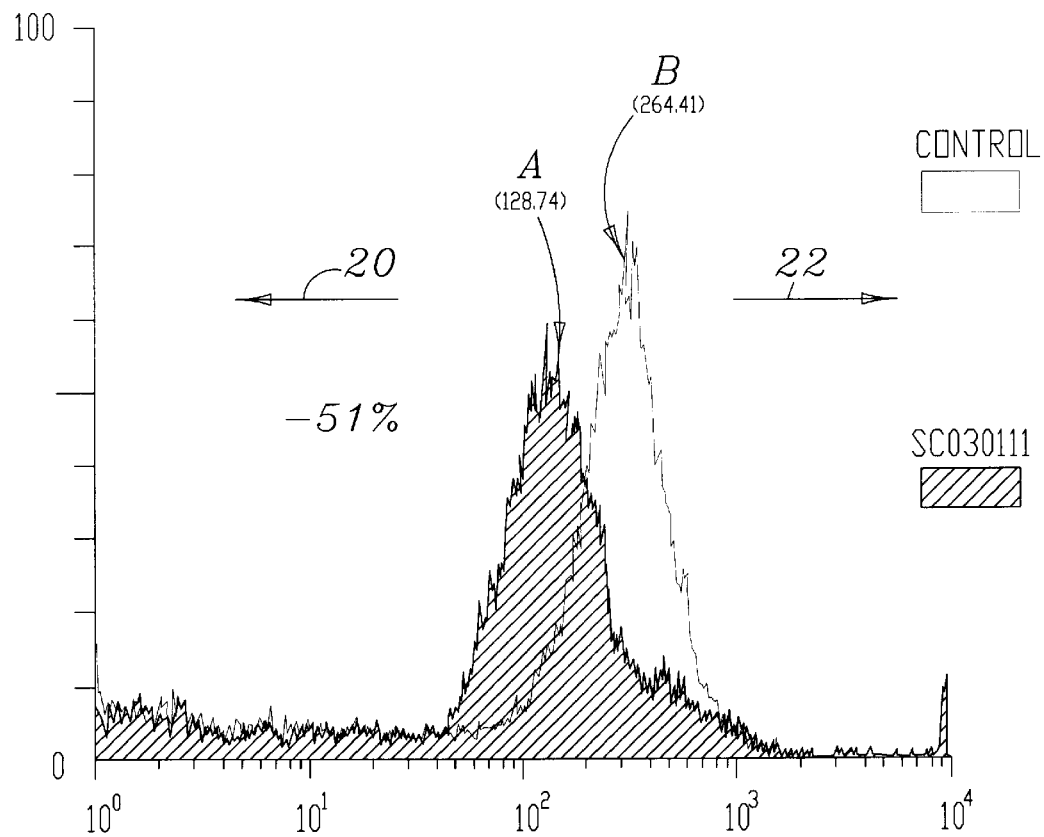
Figure 3:
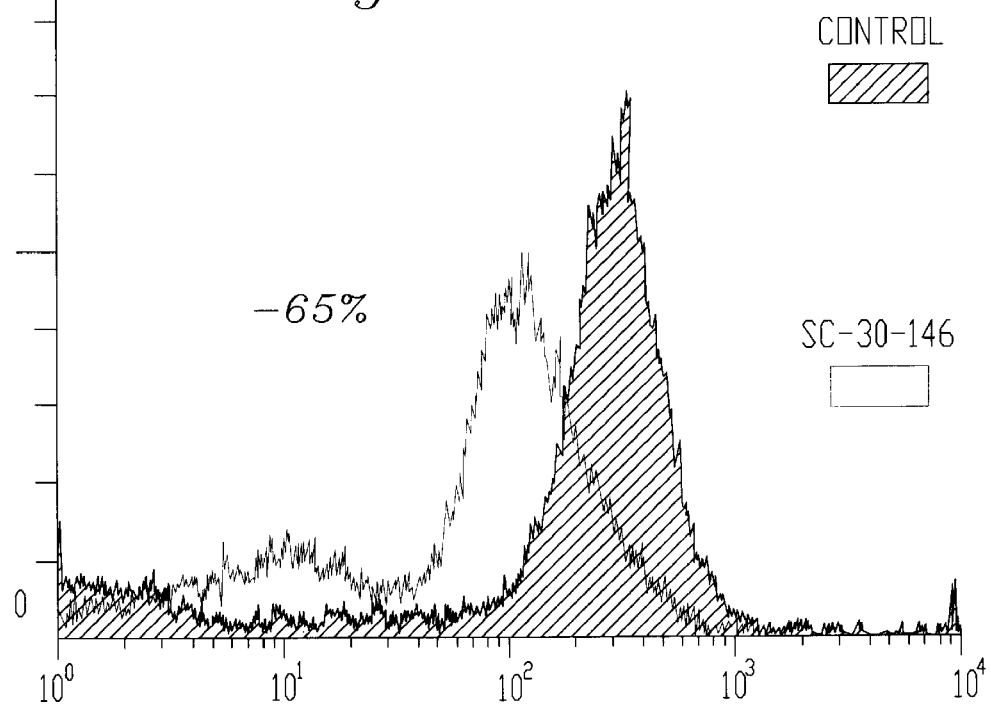

The FACscan computer was used to calculate the relative amount of antibody bound per cell using the computer generated median of the peak. FIGS. 2 and 3 provide sample curves produced by this instrumentation, and each includes a two dimensional plot of fluorescence intensity (x axis) versus relative number of cells (y axis) for the synthetic peptides SC-3-111 (Sequence ID No. 10 corresponding to an above average 51% blocking efficiency at a 4550 µM concentration) and LJCRF-1 (Sequence ID No. 6 corresponding to an above average 65% blocking efficiency at 4550 µM).

In FIG. 2, by way of example, a first SC-3-111 (Sequence ID No. 10) peptide sample median peak value at A has an intensity value of 128.74. A control sample was obtained from an identical procedure to that of the SC-3-111 (Sequence ID No. 10) sample, but one without the step of adding a synthetic peptide cocktail. A control sample median peak value at B has an intensity value of 264.41.

Accordingly, shifting of Peak A away from Peak B in the direction of arrow 20 indicates, by a reduction of cell fluorescence intensity values, that less mouse IgG anti-human CD11a is specifically bound to the T-cells. The degree of shifting was quantified by applying a calculation for percentage change:

% change=[(observed−control/(control)]* 100%; i.e.,

%change=[(128.74−264.41)/(264.41)]* 100%=−51%.

The shifting of Peak A in the negative direction of arrow 20 indicates successful antibody blocking, i.e., the peptides modulated the antibody to T-cell binding interaction by inhibiting or blocking the antibody from attaching to its complimentary LFA or ICAM target. Similarly, a shifting of Peak A in the opposite (positive) direction of arrow 22 would indicate an enhanced level of binding as compared to the control.

Figure 4:
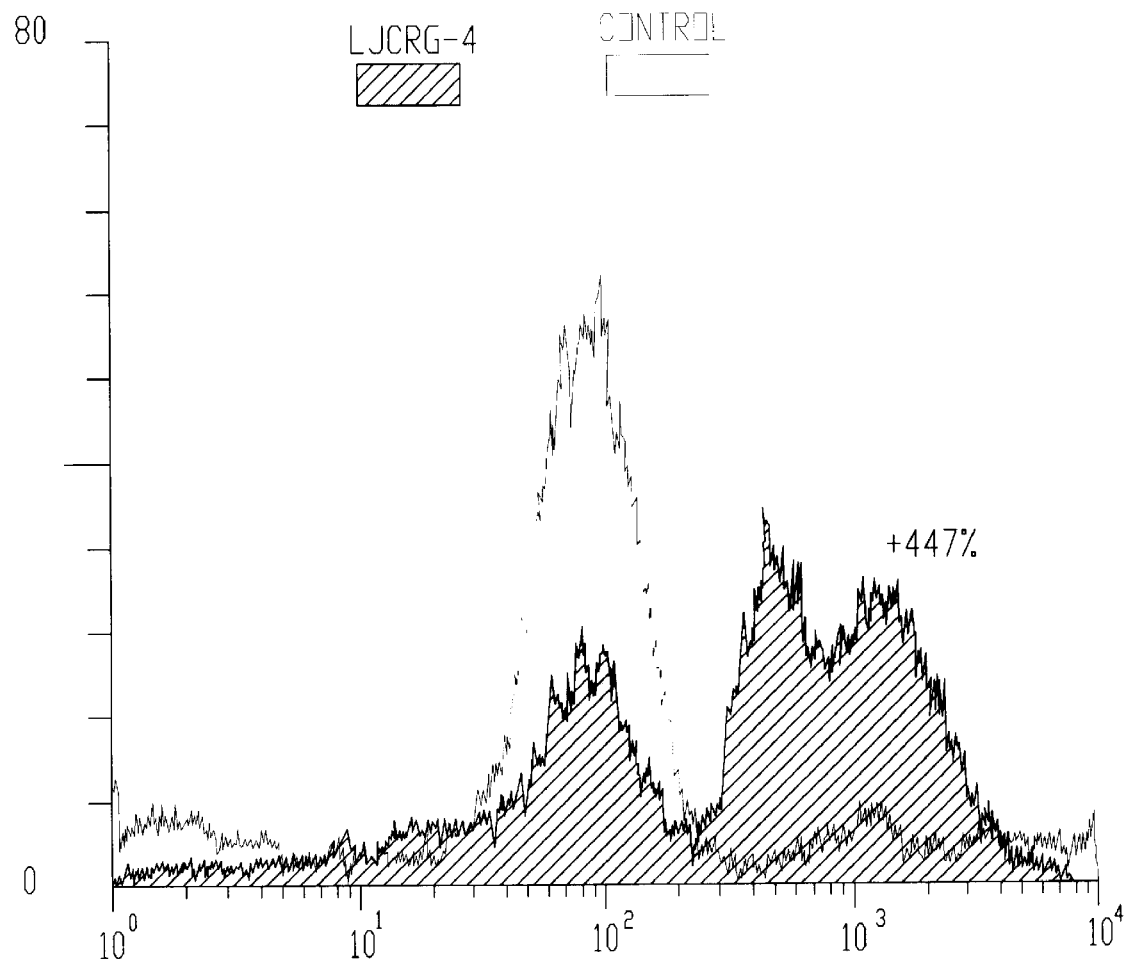

FIG. 4 (for sample LJCRF-4 at 4550 $\mu$M) is similar to FIGS. 2 and 3, but the +447% curve shift occurs in a positive direction, which indicates enhancement of the anti-ICAM antibody binding activity, not inhibition thereof.

Table 2, in part, provides a summary of the FACscan results for each of the peptides from which results were obtained. Most samples received multiple measurements, and the results varied appreciably for repeat tests within a given concentration. Accordingly, the Table 2 FACscan results include an average value for all of the median intensity peak values thus obtained; e.g., FIG. 4 depicts a +447% median peak enhancement for LJCRF-4 at 4550 $\mu$M, which was one enhancement value out of five such values that contributed to the overall average of +275±33 in Table 2. Standard error was calculated for each peptide as the standard deviation in the population of median peak intensity values divided by the square root of the number of intensity values.

The results of Table 2 indicate that several ICAM-1 or LFA-1 peptides having lengths from about 10–25 amino acid residues serve to regulate the binding of antibodies which are specific for the ligands of these peptides. For example, an ICAM-1 derived peptide such as SC-3-111 can bind with the ligand LFA-1 and inhibit the binding of a monoclonal antibody that is specific for LFA1. The LJCRF-2 peptide exhibited a capacity to block antibody binding at a 4550 $\mu$M concentration, but functioned to enhance such binding at a 2275 $\mu$M concentration.

EXAMPLE 3

Homotypic Adhesion Assay

An assay was performed to demonstrate that short-chain peptides can inhibit or enhance the intercellular adhesion between human T-cells by modulating the LFA/ICAM binding interaction between respective cells. As before, the T-cells were Molt3 cells prepared in RPMI 1640 growth medium according to Example 2. An approximate 7 ml aliquot of the growth medium was centrifuged (Jouan Model GT422 at 1400 rpm for 6.5 minutes), and the supernatant fluid was decanted. The pellet was resuspended in the supernatant fluid at titer of about 1×10$^6$ cells/ml, with the excess supernatant fluid being retained for future resuspension of the peptides.

A 228 nmol quantity of the LJCRF-1 (Sequence ID No. 6) peptide described in Table 1 was diluted with the supernatant fluid to a 500 $\mu$l final volume, and filtered in microcentrifuge filter tubes (0.22 micron filter; 3500 rpm for 6 minutes). Serial dilution of the filtered peptide with supernatant fluid was conducted to yield five 125 $\mu$l peptide solutions to give respective concentrations of about 115 $\mu$M, 230 $\mu$M, 460 $\mu$M, 910 $\mu$M, and 1.82 mM. At each concentration, a 125 $\mu$l portion of the cell suspension was pipetted into each 125 $\mu$l portion of the peptide solutions to yield combined samples having a 250 $\mu$l volume. The 250 $\mu$l samples were seeded into individual wells in a 48-well tissue culture grade plate (from Costar of Cambridge, Md.) and incubated at 37° C. for 30 minutes. Each sample received 5 $\mu$l of 2,5-methyl dihydroxy cinnamate ("MDHC") for a 10 $\mu$M final concentration, and was subsequently incubated for about 10 hours at 37° C. MDHC induces intercellular clumping of human T-cells (Tibbetts, Butler, and Benedict, submitted) by activating the LFA/ICAM binding interaction between respective cells.

Pictures were taken of five random fields per sample using an Olympus photomicroscope having a 0.8 mm field at 400× magnification, and a 3.2 mm field of view at 100× magnification. The amount of clumping observed was quantified by determining the mean number of clumps per field±a standard error.

Figure 5:
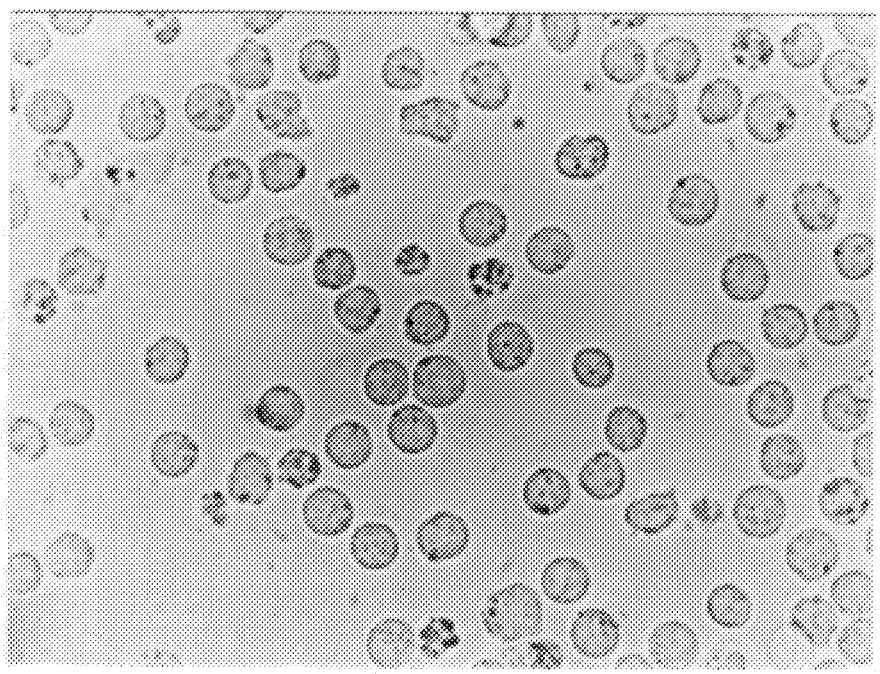
FIG. 5 is a photograph obtained from a control sample in a T-cell intercellular adhesion assay, wherein the cells demonstrated a natural lack of intercellular clumping.
Figure 6:
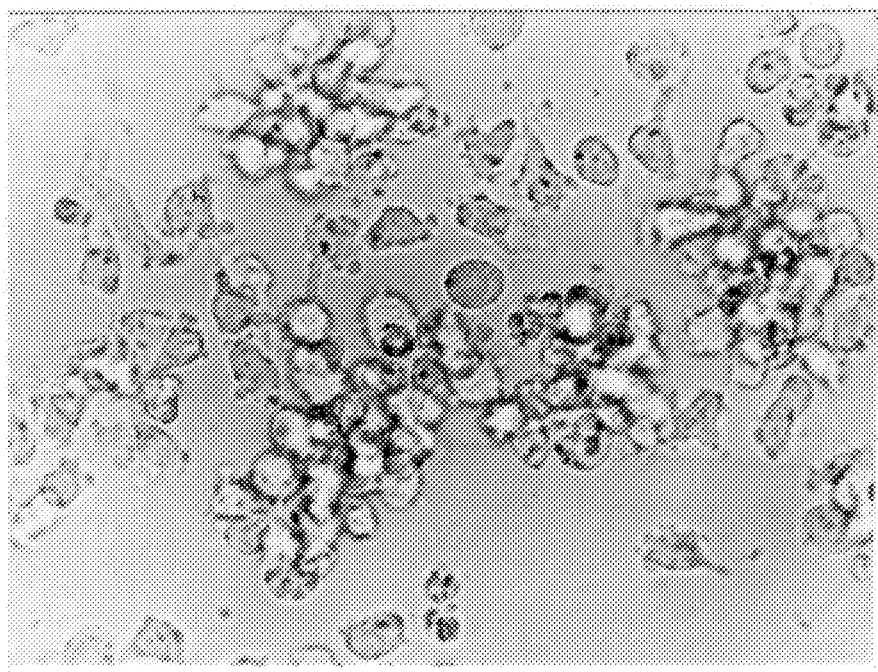
FIG. 6 is a photograph of a sample similar to that of FIG. 5, but in which a chemical additive has induced substantially complete intercellular clumping by way of the ICAM/LFA binding interaction.
Figure 7:
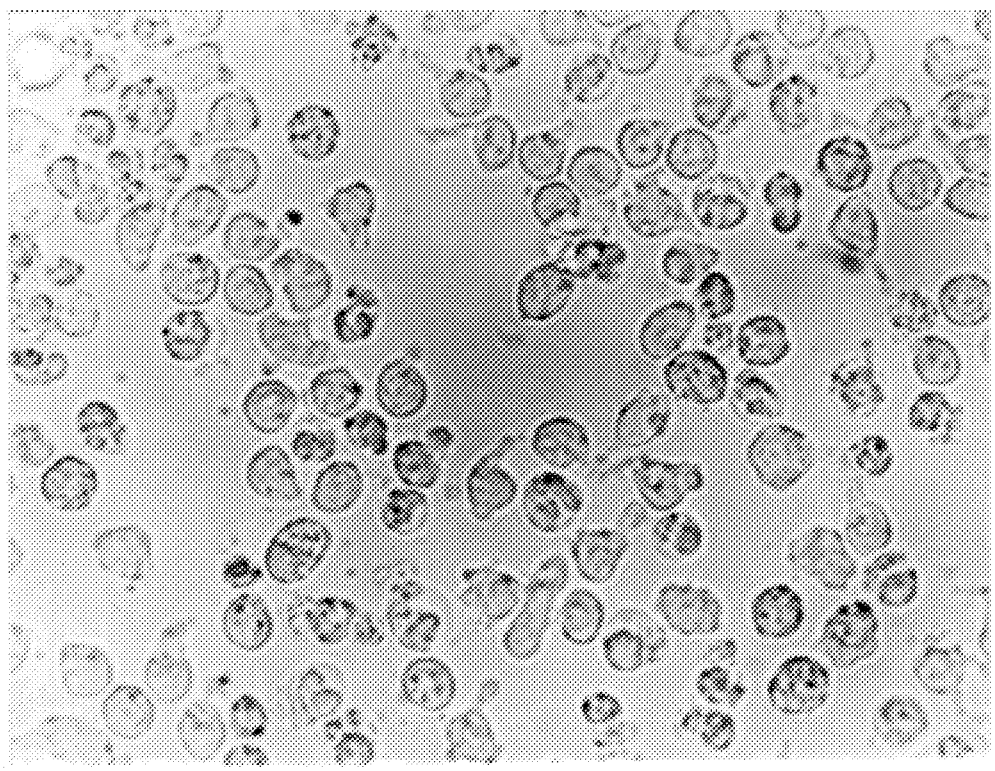
FIG. 7 is a photograph of a sample similar to that of FIG. 6, wherein a peptide of the invention has overcome the effect of the chemical additive to restore the sample to a state wherein substantially no intercellular clumping is observed.

The assay was repeatedly conducted for most of the short-chain peptides of Table 1, and these results are summarized below in Table 2. FIGS. 5, 6, and 7 replicate photographs taken from exemplary peptide assays. FIG. 5 is a photograph of the control sample having no peptides and no MDHC added, from which essentially no clumping of cells is observed. FIG. 6 depicts a photograph taken from a sample having MDHC added with no synthetic peptides, and demonstrates substantial clumping of cells. FIG. 7 depicts a photograph taken from the LJCRF-6 (Sequence ID No. 18) peptide assay at 910 $\mu$M, and demonstrates an almost total inhibition of MDHC induced clumping activity. Any sample having a score of "+++" or "++++" is considered to have a significant ability to modulate T-cell binding interaction. This is similar to results obtained by incubating similarly treated cells with antibody against either LFA or ICAM.

The homotypic adhesion assay assesses the actual ability of a candidate peptide to modulate the ability of T-cells to adhere with one another. At high concentrations, some of these peptides can function as blockers of intercellular adhesion, while having a capacity for functioning as binding enhancers at lower concentrations in growth medium; e.g., ICAM-derived LJCRF2 at respective 910 and 460 $\mu$M concentrations, and LFA-derived LJCRF-4 at respective 230 and 460 $\mu$M concentrations.

EXAMPLE 4

Cell Metabolic Assay

After taking the photographs in Example 3 (and in some instances no photographs were taken), cell metabolic activity was assessed by an MTT assay. A 37.5 $\mu$l portion of MTT dye (purchased from SIGMA of St. Louis, Mo.), i.e., 3-[4, 5-dimethyl thiazole-2yl]-2, 5-diphenyl tetrazolium bromide; thiazolyl blue) was added to each well, and incubated with the cells at 37° C. for about six hours. After incubation, a 250 $\mu$l quantity of a MTT solubilization solution (of a type that may be purchased from either Fischer Scientific of St. Louis, Mo. or BCD Labs of Lawrence, Kans.) was added to each well, and incubated with the cells at room temperature overnight. In the morning, the spectrophotometric absorption of each plate was determined at 570 nm in a microplate ELISA reader manufactured by Cambridge Technologies of Watertown, Mass., in order to assess cell viability as an indicator of potential peptide toxicity.

The MTT assay is an index of the metabolic activity of the cells; any decrease in MTT absorbance reflects a decrease in metabolic activity., or indicates cell death. Some samples indicated a decrease in metabolic activity, especially at the higher concentrations, e.g., LJCRF-5 at 1820 μM. In other samples, cellular respiration was enhanced, e.g., MC-1-80 at 910 μM. The precise reasons for the observed decrease in metabolic activity are unknown, because this decrease may be caused by a number of factors. The possible causes of a decrease in metabolic activity include peptide toxicity, peptide toxicity in combination with MDHC, a simple reduction in the cellular metabolic rate.

Another possible cause of metabolic decline is that the peptides may cause the bound T-cells to die by apoptosis in a process similar to the thymic winnowing of immature T-cells. T-cells have very specific antigen receptors that serve to recognize foreign or non-self antigen complexes, and receive a first signal when they contact their particular antigen. After this initial contact, T-cells are activated to become cytotoxic T-cells by a second signal, i.e., the LFA/ICAM binding interaction. If the second signal never arrives, the cell is never activated, and is eventually induced to die by apoptosis. The peptides may induce this type of cellular death in these leukemic T-cells which are already activated by blocking the second signal (cytotoxic activation signal). Accordingly, the peptides may be utilized to induce specific immune tolerance by causing the deaths of T-cells that recognize antigens that are present at a specific time of treatment.

EXAMPLE 5

Use of Conformation Modulator Peptides

The LJCRF-2 and LJCRF-4 peptides ("modulator peptides") of Table 1 demonstrated a significant positive intensity shift in the corresponding FACS analysis of Table 2, i.e., a positive intensity shift indicating a capacity for enhancing the LFA/ICAM interaction between the T-cells and the antibody binding interaction. Following these results, a further assay was performed to ascertain the effect of sequentially combining short-chain blocker peptides with the short-chain modulator peptides of the invention. It was discovered that a combination of specific blocker and modulator peptides significantly improves the level of observed binding enhancement as quantified by a flow cytometric assay using fluorescinated peptides.

The antibody binding assay of Example 2 was twice repeated at a peptide concentration of 4550 μM, each time substituting a 455 nmol quantity of synthetic peptide selected from the group consisting of ICAM-based peptide SC-3-111 (Sequence ID No. 10) and LFA-based peptide LJCRF-4 (Sequence ID No. 16) in respective assays. Following incubation for 30 minutes at 37° C. after introduction of the first peptides, both incubated culture were supplemented by an additional quantity of FITC-labeled RB-1-88 (Sequence ID No. 19) peptide in a quantity sufficient to provide a 1.90 μM concentration in the cell/PBS solution.

Following addition of the RB-1-88 (Sequence ID No. 19) peptide, the mixture was incubated for 30 minutes at 4° C., washed three times with 500 μl PBS/BSA, resuspended in 500 μl PBS/BSA and immediately subjected to a flow cytometer analysis as before. Table 3 presents the results of this analysis, which are also depicted in FIGS. 8 (SC-3-111) and 9 (LJCRF-4).

FIG. 9 depicts binding of RB-1-88 to T cells and the ability of LJCRF-4 to enhance the binding. Conversely, FIG. 8 demonstrates that the SC-3-111 peptide had no effect upon the ability of cell surface ICAM-1 to bind RB-1-88.

The results of Table 3 and FIG. 9 indicate that the LJCRF-4 peptide significantly enhanced the binding of RB-1-88 peptide to ICAM-1. Similar enhancement of the RB1-88 peptide binding avidity was not observed in the presence of SC-3-111 peptide, inasmuch as the negative 8% blocking shift (FIG. 8) is probably not significant in terms of laboratory error.

The peptides that serve to promote interprotein binding capacities do so according to the steps of: (1) binding to the protein ligand at a first site, and (2) changing the conformation of the protein ligand to make a second site more available for binding with the corresponding monoclonal antibody or peptide counterpart to the protein ligand. By way of example, the LFA-derived LJCRF-4 modulator peptide inherently targets a corresponding ICAM protein. The resultant enhanced ICAM/LFA-type of reactive binding must result from a conformational change, but cannot result from phosphorylation-induced conformational changes because ICAM configuration is generally not influenced by cellular phosphorylation pathways.

TABLE 2

PEPTIDE RESULTS COMPARISON

| Peptides | | | Antibody Binding (FACS Analysis) | | | Homotypic Adhesion | | | | MTT | | |
|---|---|---|---|---|---|---|---|---|---|---|---|---|
| (Sequence ID No.) | | Tests | Conc. | | | Tests | | | Conc. | Test | | Conc. |
| Peptide | Derivation | Run | [μM] | Fluorescence[1] | mAb | Run | Effect | Amount | [μM] | Runs | % Viability | [μM] |
| SC-3-111 | ICAM-1 | 11 | 4550 | −29 ± 2 | CD11a | 3 | Block | +++ | 1820 | 3 | 69 | 1820 |
| (10) | | 6 | 2275 | −12 ± 4 | CD11a | 3 | Block | ++++ | 910 | 3 | 89 | 910 |
| | | | | | | 1 | Block | ++ | 460 | 2 | 95 | 460 |
| | | | | | | 1 | Block | + | 230 | 2 | 93 | 230 |
| | | | | | | | | | | 2 | 85 | |
| LJCRF-1 | ICAM-1 | 8 | 4550 | −29 ± 3 | CD11a | 2 | Block | +++ | 1820 | 2 | 66 | 1820 |
| (6) | | 6 | 2275 | −12 ± 2 | CD11a | 2 | Block | ++ | 910 | 2 | 92 | 910 |
| | | | | | | 1 | Block | +++ | 460 | 2 | 93 | 460 |
| | | | | | | | | | | 1 | 94 | |
| | | | | | | | | | | 1 | 112 | |
| SC-3-152 | ICAM-1 | 5 | 4550 | −43 ± 7 | CD11a | 2 | Block | ++++ | 1820 | 2 | 43 | 1820 |
| LJCRF-2 | | 4 | 2275 | +48 ± 8 | CD11a | 1 | Block | +++ | 910 | 2 | 38 | 910 |
| (11) | | | | | | 1 | Enhance | ++ | 460 | 2 | 38 | 460 |
| | | | | | | 1 | Enhance | +++ | 230 | 2 | 38 | 230 |

TABLE 2-continued

PEPTIDE RESULTS COMPARISON

| Peptides | | Antibody Binding (FACS Analysis) | | | | Homotypic Adhesion | | | | MTT | | |
|---|---|---|---|---|---|---|---|---|---|---|---|---|
| (Sequence ID No.) | | Tests | Conc. | | | Tests | | | Conc. | Test | | Conc. |
| Peptide | Derivation | Run | [μM] | Fluorescence[1] | mAb | Run | Effect | Amount | [μM] | Runs | % Viability | [μM] |
| LJCRF-3 (12) | ICAM-1 | 2 | 4550 | −13 ± 19 | CD11a | | | | | 2<br>1<br>1<br>1<br>1 | 38<br>111<br>109<br>111<br>97 | |
| MC-1-80 (9) | ICAM-1 | | | | | | | | | 1<br>1<br>1<br>1 | 125<br>108<br>89<br>110 | |
| LJCRF-4 (16) | LFA-1β | 1<br>5<br>2 | 6825<br>4550<br>2275 | +521<br>+275 ± 33<br>+3 ± 1 | CD54<br>CD54<br>CD54 | 1<br>1<br>1<br>1<br>1 | Block<br>Block<br>Block<br>Enhance<br>Enhance | +++<br>++++<br>++++<br>+++<br>+++ | 1820<br>910<br>460<br>230<br>115 | 2<br>3<br>3<br>3<br>3 | 11<br>60<br>94<br>101<br>99 | 1820<br>910<br>460<br>230<br>115 |
| SC-3-223 [Identical to LJCRF-4] (16) | LFA-1β | | | | | 2<br>2<br>1<br>1<br>1 | Block<br>Block<br>Block<br>Block<br>Block | ++++<br>++++<br>+++<br>+++<br>++ | 1820<br>910<br>460<br>230<br>115 | 1<br>1<br>1<br>1<br>1 | 75<br>108<br>112<br>109<br>103 | 1820<br>910<br>460<br>230<br>115 |
| LJCRF-5 (17) | LFA-1α | 1 | 4550 | −17 | CD54 | 1<br>1<br>1<br>1<br>1 | Block<br>Block<br>Block<br>Block<br>Block | ++++<br>++++<br>++<br>++<br>++ | 1820<br>910<br>460<br>230<br>115 | 3<br>3<br>2<br>2<br>2 | 20<br>52<br>81<br>84<br>95 | 1820<br>910<br>460<br>230<br>115 |
| LJCRF-6 (18) | LFA-1α insert | 1 | 4550 | −4 | CD54 | 1 | Block | +++ | 1820 | 1<br>1<br>1<br>1 | 111<br>109<br>111<br>97 | 1820 |

[1] % change from control of the medium fluorescence intensity

TABLE 3

SEQUENTIALLY COMBINED BLOCKER AND MODULATOR PEPTIDES

| Peptide | Sequence ID | FACS Analysis (RB-1-88 binding) |
|---|---|---|
| SC-3-111 | 10 | −8 |
| LJCRF-4 | 16 | +145 |

---

We Claim:

1. A modulator peptide, wherein the modulator peptide, when bound to a human ICAM-1 molecule, increases the binding affinity of a blocking peptide for the ICAM-1 molecule by inducing a conformational change in the ICAM-1 molecule, and the blocking peptide, when bound to the ICAM-1 molecule, inhibits the binding of the ICAM-1 molecule to a human LFA-1 molecule, wherein the modulator peptide comprises an amino acid sequence included in the amino acid sequence of the extracellular segment of the LFA-1 molecule and has a molecular weight under 20 kilodaltons, wherein the modulator peptide is prepared by a method comprising the steps of:

(a) identifying a protein domain of the LFA-1 molecule wherein the protein domain is capable of binding to the ICAM-1 molecule; and (b) synthesizing the modulator peptide comprising an amino acid sequence included in the protein domain, wherein, in the binding assay of Example 2, the fluorescence intensity value calculated using a first sample lacking the modulator peptide is at least 10% lower than the fluorescence intensity value calculated using a second sample including the modulator peptide.

2. A modulator peptide, wherein the modulator peptide, when bound to a human ICAM-1 molecule, increases the binding affinity of a blocking peptide for the ICAM-1 molecule by inducing a conformational change in the ICAM-1 molecule, and the blocking peptide, when bound to the ICAM-1 molecule, inhibits the binding of the ICAM-1 molecule to a human LFA-1 molecule, and wherein the modulator peptide comprising Sequence ID No. 16.

3. A modulator peptide, wherein the modulator peptide, when bound to a human LFA-1 molecule, increases the binding affinity of a blocking peptide for the LFA-1 molecule by inducing a conformational change in the LFA-1 molecule, and the blocking peptide, when bound to the LFA-1 molecule, inhibits the binding of the LFA-1 molecule to a human ICAM-1 molecule, wherein the modulator peptide comprises an amino acid sequence included in the amino acid sequence of the extracellular segment of the ICAM-1 molecule and has a molecular weight under 20 kilodaltons, wherein the modulator peptide is prepared by a method comprising the steps of:
  (a) identifying a protein domain of the ICAM-1 molecule wherein the protein domain is capable of binding to the LFA-1 molecule; and
  (b) synthesizing the modulator peptide comprising an amino acid sequence included in the protein domain, and
wherein, in the binding assay of Example 2, the fluorescence intensity value calculated using a first sample lacking the modulator peptide is at least 10% lower than the fluorescence intensity value calculated using a second sample including the modulator peptide.

4. A modulator peptide, wherein the modulator peptide, when bound to a human LFA-1 molecule, increases the binding affinity of a blocking peptide for the LFA-1 molecule by inducing a conformational change in the LFA-1 molecule, and the blocking peptide, when bound to the LFA-1 molecule, inhibits the binding of the LFA-1 molecule to a human ICAM-1 molecule, and wherein the modulator peptide comprises amino acid Sequence ID No. 11.

5. A peptide composition effective in inhibiting the binding of a human ICAM-1 molecule to a human LFA-1 molecule, wherein the peptide composition comprises:

a blocking peptide, wherein the blocking peptide has an initial binding affinity for the ICAM-1 molecule, and, when bound to the ICAM-1 molecule, inhibits the binding of the ICAM-1 molecule to the LFA-1 molecule; and a modulator peptide, wherein the modulator peptide, when bound to the ICAM-1 molecule, increases the binding affinity of the blocking peptide for the ICAM-1 molecule by inducing a conformational change in the ICAM-1 molecule, wherein the blocking peptide and the modulator peptide each comprise an amino acid sequence included in the amino acid sequence of the extracellular segment of the LFA-1 molecule and each have molecular weights of under 20 kilodaltons, wherein the blocking peptide is prepared by a method comprising the steps of:

(a) identifying a first protein domain of the LFA-1 molecule wherein the first protein domain is capable of binding to the ICAM-1 molecule; and (b) synthesizing a blocking peptide comprising an amino acid sequence included in the first protein domain, wherein, in the antibody-binding assay of Example 2, the fluorescence intensity value calculated using a first sample lacking the blocking peptide is at least 10% higher than the fluorescence intensity value calculated using a second sample including the blocking peptide, wherein the modulator peptide is prepared by a method comprising the steps of:

(c) identifying a second protein domain of the LFA-1 molecule wherein the second protein domain is capable of binding to the ICAM-1 molecule; and (d) synthesizing the modulator peptide comprising an amino acid sequence included in the second protein domain, wherein, in the binding assay of Example 2, the fluorescence intensity value calculated using a first sample lacking the modulator peptide is at least 10% lower than the fluorescence intensity value calculated using a second sample including the modulator peptide.

6. The peptide composition of claim 5, wherein the blocking peptide comprises an amino acid sequence selected from the group consisting of Sequence ID Nos. 17, and 18.

7. A peptide composition effective in inhibiting the binding of a human ICAM-1 molecule to a human LFA-1 molecule, wherein the peptide composition comprises:

a blocking peptide, wherein the blocking peptide has an initial binding affinity for the ICAM-1 molecule, and, when bound to the ICAM-1 molecule, inhibits the binding of the ICAM-1 molecule to the LFA-1 molecule; and a modulator peptide, wherein the modulator peptide, when bound to the ICAM-1 molecule, increases the binding affinity of the blocking peptide for the ICAM-1 molecule by inducing a conformational change in the ICAM-1 molecule, wherein the blocking peptide comprises an amino acid sequence included in the amino acid sequence of the extracellular segment of the LFA-1 molecule and each have molecular weights of under 20 kilodaltons, wherein the modulator peptide comprises the amino acid sequence of Sequence ID No. 16, wherein the blocking peptide is prepared by a method comprising the steps of:

(a) identifying a first protein domain of the LFA-1 molecule wherein the first protein domain is capable of binding to the ICAM-1 molecule; and (b) synthesizing a blocking peptide comprising an amino acid sequence included in the first protein domain, and wherein, in the antibody-binding assay of Example 2, the fluorescence intensity value calculated using a first sample lacking the blocking peptide is at least 10% higher than the fluorescence intensity value calculated using a second sample including the blocking peptide.

8. A peptide composition effective in inhibiting the binding of a human LFA-1 molecule to a human ICAM-1 molecule, wherein the peptide composition comprises:

a blocking peptide, wherein the blocking peptide has an initial binding affinity for the LFA-1 molecule, and, when bound to the LFA-1 molecule, inhibits the binding of the LFA-1 molecule to the ICAM-1 molecule; and a modulator peptide, wherein the modulator peptide, when bound to the LFA-1 molecule, increases the binding affinity of the blocking peptide for the LFA-1 molecule by inducing a conformational change in the LFA-1 molecule, wherein the blocking peptide and the modulator peptide each comprise an amino acid sequence included in the amino acid sequence of the extracellular segment of the ICAM-1 molecule and each have molecular weights of under 20 kilodaltons, wherein the blocking peptide is prepared by a method comprising the steps of:
(a) identifying a first protein domain of the ICAM-1 molecule wherein the first protein domain is capable of binding to the LFA-1 molecule; and
(b) synthesizing a blocking peptide comprising an amino acid sequence included in the first protein domain, wherein, in the antibody-binding assay of Example 2, the fluorescence intensity value calculated using a first sample lacking the blocking peptide is at least 10% higher than the fluorescence intensity value calculated using a second sample including the blocking peptide, wherein the modulator peptide is prepared by a method comprising the steps of:
(c) identifying a second protein domain of the ICAM-1 molecule wherein the second protein domain is capable of binding to the LFA-1 molecule; and
(d) synthesizing the modulator peptide comprising an amino acid sequence included in the second protein domain, wherein, in the binding assay of Example 2, the fluorescence intensity value calculated using a first sample lacking the modulator peptide is at least 10% lower than the fluorescence intensity value calculated using a second sample including the modulator peptide.

9. The peptide composition of claim 8, wherein the blocking peptide comprises Sequence ID No. 6.

10. A peptide composition effective in inhibiting the binding of a human LFA-1 molecule to a human ICAM-1 molecule, wherein the peptide composition comprises:

a blocking peptide, wherein the blocking peptide has an initial binding affinity for the LFA-1 molecule, and, when bound to the LFA-1 molecule, inhibits the binding of the LFA-1 molecule to the ICAM-1 molecule; and a modulator peptide, wherein the modulator peptide, when bound to the LFA-1 molecule, increases the binding affinity of the blocking peptide for the LFA-1 molecule by inducing a conformational change in the LFA-1 molecule, wherein the blocking peptide comprises an amino acid sequence included in the amino acid sequence of the extracellular segment of the ICAM-1 molecule and each have molecular weights of under 20 kilodaltons, wherein the modulator peptide comprises the amino acid sequence of Sequence ID No. 11, wherein the blocking peptide is prepared by a method comprising the steps of:
(a) identifying a first protein domain of the ICAM-1 molecule wherein the first protein domain is capable of binding to the LFA-1 molecule; and
(b) synthesizing a blocking peptide comprising an amino acid sequence included in the first protein domain, and wherein, in the antibody-binding assay of Example 2, the fluorescence intensity value calculated using a first sample lacking the blocking peptide is at least 10% higher than the fluorescence intensity value calculated using a second sample including the blocking peptide.

11. The peptide of Sequence ID No. 11.

12. The peptide of Sequence ID No. 16.

13. A peptide composition operable for inhibiting the interaction between ICAM-1 and LFA-1, said composition comprising:

a blocking peptide comprising a first amino acid sequence of the extracellular segment of one of the human LFA-1 or human ICAM-1 molecule and having a molecular weight of under 20 kilodaltons, said blocking peptide being capable of binding to a target molecule, which is the other of said human LFA-1 or human ICAM-1 molecule, for inhibiting said LFA-1/ICAM-1 interaction, said blocking peptide characterized by the property of having a fluorescence intensity value calculated using a first sample lacking said blocking peptide at least 10% higher than the fluorescence intensity value calculated using a second sample including said blocking peptide, in the antibody-binding assay conducted as described in Example 2; and a modulator peptide comprising a second amino acid sequence of the extracellular segment of said one of the human LFA-1 or human ICAM-1 molecule which is different than said first sequence, and having a molecular weight of under 20 kilodaltons, said modulator peptide being capable of binding to said target molecule for increasing the affinity of said blocking peptide for said target molecule, said modulator peptide characterized by the property of having a fluorescence intensity value calculated using a first sample lacking said modulator peptide of at least 10% lower than the fluorescence intensity value calculated using a second sample including said modulator peptide in the binding assay of Example 2.

14. The peptide composition of claim 13, said one of said human LFA-1 or human ICAM-1 molecule being LFA-1, and said target molecule being ICAM-1.

15. The peptide composition of claim 13, said one of said human LFA-1 or human ICAM-1 molecule being ICAM-1, and said target molecule being LFA-1.

16. The peptide composition of claim 13, said blocking peptide being selected from the group consisting of Sequence ID Nos. 6, 17, and 18.

17. The peptide composition of claim 13, said modulator peptide being selected from the group consisting of Sequence ID Nos. 11 and 16.

18. The peptide composition of claim 13, said composition having a single blocker peptide and a single modulator peptide.

19. A modulator peptide operable for enhancing the interaction between ICAM-1 and LFA-1 and comprising an amino acid sequence of the extracellular segment of one of the human LFA-1 or human ICAM-1 molecule and having a molecular weight of under 20 kDa, said modulator being capable of binding to a target molecule which is the other of said human LFA-1 or human ICAM-1 molecule, said modulator peptide characterized by the property of having a fluorescence intensity value calculated using a first sample lacking said modulator peptide of at least 10% lower than the fluorescence intensity value calculated using a second sample including said modulator peptide, in the binding assay of Example 2.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 769 amino acids
        ( B ) TYPE: amino acid
        ( D ) TOPOLOGY: both ( i i ) MOLECULE TYPE: protein ( i i i ) HYPOTHETICAL: NO ( v i ) ORIGINAL SOURCE:
    ( A ) ORGANISM: Homo sapiens
    ( F ) TISSUE TYPE: Tonsil ( i x ) FEATURE:
    ( A ) NAME/KEY: Region
    ( B ) LOCATION: 1..22
    ( D ) OTHER INFORMATION: /label=signal
        / note= "signal sequence"

( i x ) FEATURE:
    ( A ) NAME/KEY: Region
    ( B ) LOCATION: 449..496
    ( D ) OTHER INFORMATION: /label=repeat
        / note= "cysteine rich repeat"

( i x ) FEATURE:
    ( A ) NAME/KEY: Region
    ( B ) LOCATION: 497..540
    ( D ) OTHER INFORMATION: /label=repeat
        / note= "cysteine rich repeat"

( i x ) FEATURE:
    ( A ) NAME/KEY: Region
    ( B ) LOCATION: 541..581
    ( D ) OTHER INFORMATION: /label=repeat
        / note= "cysteine rich repeat"

( i x ) FEATURE:
    ( A ) NAME/KEY: Region
    ( B ) LOCATION: 582..617
    ( D ) OTHER INFORMATION: /label=repeat
        / note= "cysteine rich repeat"

( i x ) FEATURE:
    ( A ) NAME/KEY: Domain
    ( B ) LOCATION: 701..723
    ( D ) OTHER INFORMATION: /label=trans
        / note= "transmembrane domain"

( i x ) FEATURE:
    ( A ) NAME/KEY: Domain
    ( B ) LOCATION: 724..769
    ( D ) OTHER INFORMATION: /label=cyto
        / note= "cytoplasmic domain"

( x ) PUBLICATION INFORMATION:
    ( A ) AUTHORS: Pigott,
        Power,
    ( B ) TITLE: LFA-1 Amino acid sequence (B2) (from human
        tonsil)
    ( C ) JOURNAL: The Adhesion Molecule Facts Book
    ( F ) PAGES: 96-96
    ( G ) DATE: 1993
    ( K ) RELEVANT RESIDUES IN SEQ ID NO:1: FROM 1 TO 769

( x i ) SEQUENCE DESCRIPTION: SEQ ID NO:1:

```
Met Leu Gly Leu Arg Pro Pro Leu Leu Ala Leu Val Gly Leu Leu Ser
1               5                   10                  15

Leu Gly Cys Val Leu Ser Gln Glu Cys Thr Lys Phe Lys Val Ser Ser
                20                  25                  30

Cys Arg Glu Cys Ile Glu Ser Gly Pro Gly Cys Thr Trp Cys Gln Lys
            35                  40                  45

Leu Asn Phe Thr Gly Pro Gly Asp Pro Asp Ser Ile Arg Cys Asp Thr
        50                  55                  60

Arg Pro Gln Leu Leu Met Arg Gly Cys Ala Ala Asp Asp Ile Met Asp
65                  70                  75                  80

Pro Thr Ser Leu Ala Glu Thr Gln Glu Asp His Asn Gly Gly Gln Lys
                85                  90                  95

Gln Leu Ser Pro Gln Lys Val Thr Leu Tyr Leu Arg Pro Gly Gln Ala
```

-continued

|   |   |   | 100 |   |   |   | 105 |   |   |   | 110 |   |   |
|---|---|---|---|---|---|---|---|---|---|---|---|---|---|
| Ala | Ala | Phe 115 | Asn | Val | Thr | Phe | Arg 120 | Arg | Ala | Lys | Gly | Tyr 125 | Pro | Ile | Asp |
| Leu | Tyr 130 | Tyr | Leu | Met | Asp 135 | Leu | Ser | Tyr | Ser | Met 140 | Leu | Asp | Asp | Leu | Arg |
| Asn 145 | Val | Lys | Lys | Leu 150 | Gly | Gly | Asp | Leu | Leu 155 | Arg | Ala | Leu | Asn | Glu | Ile 160 |
| Thr | Glu | Ser | Gly | Arg 165 | Ile | Gly | Phe | Gly | Ser 170 | Phe | Val | Asp | Lys | Thr 175 | Val |
| Leu | Pro | Phe | Val 180 | Asn | Thr | His | Pro | Asp 185 | Lys | Leu | Arg | Asn | Pro 190 | Cys | Pro |
| Asn | Lys 195 | Glu | Lys | Glu | Cys | Gln 200 | Pro | Pro | Phe | Ala | Phe 205 | Arg | His | Val | Leu |
| Lys | Leu | Thr 210 | Asn | Asn | Ser | Asn 215 | Gln | Phe | Gln | Thr | Glu 220 | Val | Gly | Lys | Gln |
| Leu | Ile | Ser 225 | Gly | Asn | Leu | Asp 230 | Ala | Pro | Glu | Gly 235 | Gly | Leu | Asp | Ala | Met 240 |
| Met | Gln | Val | Ala | Ala 245 | Cys | Pro | Glu | Glu | Ile 250 | Gly | Trp | Arg | Asn | Val 255 | Thr |
| Arg | Leu | Leu | Val 260 | Phe | Ala | Thr | Asp | Asp 265 | Gly | Phe | His | Phe | Ala 270 | Gly | Asp |
| Gly | Lys | Leu 275 | Gly | Ala | Ile | Leu | Thr 280 | Pro | Asn | Asp | Gly | Arg 285 | Cys | His | Leu |
| Glu | Asp 290 | Asn | Leu | Tyr | Lys | Arg 295 | Ser | Asn | Glu | Phe | Asp 300 | Tyr | Pro | Ser | Val |
| Gly 305 | Gln | Leu | Ala | His | Lys 310 | Leu | Ala | Glu | Asn | Asn 315 | Ile | Gln | Pro | Ile | Phe 320 |
| Ala | Val | Thr | Ser | Arg 325 | Met | Val | Lys | Thr | Tyr 330 | Glu | Lys | Leu | Thr | Glu 335 | Ile |
| Ile | Pro | Lys | Ser | Ala 340 | Val | Gly | Glu | Leu 345 | Ser | Glu | Asp | Ser | Ser 350 | Asn | Val |
| Val | His | Leu 355 | Ile | Lys | Asn | Ala | Tyr 360 | Asn | Lys | Leu | Ser | Ser 365 | Arg | Val | Phe |
| Leu | Asp 370 | His | Asn | Ala | Leu | Pro 375 | Asp | Thr | Leu | Lys | Val 380 | Thr | Tyr | Asp | Ser |
| Phe 385 | Cys | Ser | Asn | Gly | Val 390 | Thr | His | Arg | Asn | Gln 395 | Pro | Arg | Gly | Asp | Cys 400 |
| Asp | Gly | Val | Gln | Ile 405 | Asn | Val | Pro | Ile | Thr 410 | Phe | Gln | Val | Lys | Val 415 | Thr |
| Ala | Thr | Glu | Cys 420 | Ile | Gln | Glu | Gln | Ser 425 | Phe | Val | Ile | Arg | Ala 430 | Leu | Gly |
| Phe | Thr | Asp 435 | Ile | Val | Thr | Val | Gln 440 | Val | Leu | Pro | Gln | Cys 445 | Glu | Cys | Arg |
| Cys | Arg 450 | Asp | Gln | Ser | Arg | Asp 455 | Arg | Ser | Leu | Cys | His 460 | Gly | Lys | Gly | Phe |
| Leu 465 | Glu | Cys | Gly | Ile | Cys 470 | Arg | Cys | Asp | Thr | Gly 475 | Tyr | Ile | Gly | Lys | Asn 480 |
| Cys | Glu | Cys | Gln | Thr 485 | Gln | Gly | Arg | Ser | Ser 490 | Gln | Glu | Leu | Glu | Gly 495 | Ser |
| Cys | Arg | Lys | Asp 500 | Asn | Asn | Ser | Ile | Ile 505 | Cys | Ser | Gly | Leu | Gly 510 | Asp | Cys |
| Val | Cys | Gly 515 | Gln | Cys | Leu | Cys | His 520 | Thr | Ser | Asp | Val | Pro 525 | Gly | Lys | Leu |

| | | | | | | | | | | | | | | |
|---|---|---|---|---|---|---|---|---|---|---|---|---|---|---|
| Ile | Tyr | Gly | Gln | Tyr | Cys | Glu | Cys | Asp | Thr | Ile | Asn | Cys | Glu | Arg | Tyr |
| | 530 | | | | | 535 | | | | 540 | | | | | |
| Asn | Gly | Gln | Val | Cys | Gly | Gly | Pro | Gly | Arg | Gly | Leu | Cys | Phe | Cys | Gly |
| 545 | | | | | 550 | | | | | 555 | | | | | 560 |
| Lys | Cys | Arg | Cys | His | Pro | Gly | Phe | Glu | Gly | Ser | Ala | Cys | Gln | Cys | Glu |
| | | | | 565 | | | | | 570 | | | | | 575 | |
| Arg | Thr | Thr | Glu | Gly | Cys | Leu | Asn | Pro | Arg | Arg | Val | Glu | Cys | Ser | Gly |
| | | | 580 | | | | | 585 | | | | | 590 | | |
| Arg | Gly | Arg | Cys | Arg | Cys | Asn | Val | Cys | Glu | Cys | His | Ser | Gly | Tyr | Gln |
| | | 595 | | | | | 600 | | | | | 605 | | | |
| Leu | Pro | Leu | Cys | Gln | Glu | Cys | Pro | Gly | Cys | Pro | Ser | Pro | Cys | Gly | Lys |
| | 610 | | | | | 615 | | | | | 620 | | | | |
| Tyr | Ile | Ser | Cys | Ala | Glu | Cys | Leu | Lys | Phe | Glu | Lys | Gly | Pro | Phe | Gly |
| 625 | | | | | 630 | | | | | 635 | | | | | 640 |
| Lys | Asn | Cys | Ser | Ala | Ala | Cys | Pro | Gly | Leu | Gln | Leu | Ser | Asn | Asn | Pro |
| | | | | 645 | | | | | 650 | | | | | 655 | |
| Val | Lys | Gly | Arg | Thr | Cys | Lys | Glu | Arg | Asp | Ser | Glu | Gly | Cys | Trp | Val |
| | | | 660 | | | | | 665 | | | | | 670 | | |
| Ala | Tyr | Thr | Leu | Glu | Gln | Gln | Asp | Gly | Met | Asp | Arg | Tyr | Leu | Ile | Tyr |
| | | 675 | | | | | 680 | | | | | 685 | | | |
| Val | Asp | Glu | Ser | Arg | Glu | Cys | Val | Ala | Gly | Pro | Asn | Ile | Ala | Ala | Ile |
| | 690 | | | | | 695 | | | | | 700 | | | | |
| Val | Gly | Gly | Thr | Val | Ala | Gly | Ile | Val | Leu | Ile | Gly | Ile | Leu | Leu | Leu |
| 705 | | | | | 710 | | | | | 715 | | | | | 720 |
| Val | Ile | Trp | Lys | Ala | Leu | Ile | His | Leu | Ser | Asp | Leu | Arg | Glu | Tyr | Arg |
| | | | | 725 | | | | | 730 | | | | | 735 | |
| Arg | Phe | Glu | Lys | Glu | Lys | Leu | Lys | Ser | Gln | Trp | Asn | Asn | Asp | Asn | Pro |
| | | | 740 | | | | | 745 | | | | | 750 | | |
| Leu | Phe | Lys | Ser | Ala | Thr | Thr | Thr | Val | Met | Asn | Pro | Lys | Phe | Ala | Glu |
| | | 755 | | | | | 760 | | | | | 765 | | | |
| Ser | | | | | | | | | | | | | | | |

( 2 ) INFORMATION FOR SEQ ID NO:2:

( i ) SEQUENCE CHARACTERISTICS:
        ( A ) LENGTH: 1170 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Homo sapiens
        ( G ) CELL TYPE: T-cell
        ( H ) CELL LINE: HL-60

( i x ) FEATURE:
        ( A ) NAME/KEY: Region
        ( B ) LOCATION: 1..25
        ( D ) OTHER INFORMATION: /label=signal
            / note= "Signal sequence"

( i x ) FEATURE:
        ( A ) NAME/KEY: Region
        ( B ) LOCATION: 32..79
        ( D ) OTHER INFORMATION: /label=Repeat
            / note= "Repeat I"

( i x ) FEATURE:
        ( A ) NAME/KEY: Region
        ( B ) LOCATION: 82..132
        ( D ) OTHER INFORMATION: /label=Repeat -continued

```
                / note= "Repeat II"

( i x ) FEATURE:
          ( A ) NAME/KEY: Region
          ( B ) LOCATION: 339..391
          ( D ) OTHER INFORMATION: /label=Repeat
                / note= "Repeat III"

( i x ) FEATURE:
          ( A ) NAME/KEY: Region
          ( B ) LOCATION: 392..446
          ( D ) OTHER INFORMATION: /label=Repeat
                / note= "Repeat IV"

( i x ) FEATURE:
          ( A ) NAME/KEY: Region
          ( B ) LOCATION: 447..508
          ( D ) OTHER INFORMATION: /label=Repeat
                / note= "Repeat V"

( i x ) FEATURE:
          ( A ) NAME/KEY: Region
          ( B ) LOCATION: 509..567
          ( D ) OTHER INFORMATION: /label=Repeat
                / note= "Repeat VI"

( i x ) FEATURE:
          ( A ) NAME/KEY: Region
          ( B ) LOCATION: 568..629
          ( D ) OTHER INFORMATION: /label=Repeat
                / note= "Repeat VII"

( i x ) FEATURE:
          ( A ) NAME/KEY: Domain
          ( B ) LOCATION: 170..349
          ( D ) OTHER INFORMATION: /label=IDomain
                / note= "I-Domain"

( i x ) FEATURE:
          ( A ) NAME/KEY: Domain
          ( B ) LOCATION: 1089..1112
          ( D ) OTHER INFORMATION: /label=Trans
                / note= "Transmembrane Domain"

( i x ) FEATURE:
          ( A ) NAME/KEY: Domain
          ( B ) LOCATION: 1113..1170
          ( D ) OTHER INFORMATION: /label=Cyto
                / note= "Cytoplasmic domain"

( x ) PUBLICATION INFORMATION:
          ( A ) AUTHORS: Pigott,
                Power,
          ( B ) TITLE: LFA-1 Amino acid sequence (alphaL) (from
                PMA- stimulated HL-60 cells)
          ( C ) JOURNAL: The Adhesion Molecule Facts Book
          ( F ) PAGES: 94-95
          ( G ) DATE: 1993
          ( K ) RELEVANT RESIDUES IN SEQ ID NO:2: FROM 1 TO 1170

( x i ) SEQUENCE DESCRIPTION: SEQ ID NO:2:

Met   Lys   Asp   Ser   Cys   Ile   Thr   Val   Met   Ala   Met   Ala   Leu   Leu   Ser   Gly
 1                       5                       10                            15

Phe   Phe   Phe   Phe   Ala   Pro   Ala   Ser   Ser   Tyr   Asn   Leu   Asp   Val   Arg   Gly
                  20                      25                            30

Ala   Arg   Ser   Phe   Ser   Pro   Pro   Arg   Ala   Gly   Arg   His   Phe   Gly   Tyr   Arg
            35                      40                      45

Val   Leu   Gln   Val   Gly   Asn   Gly   Val   Ile   Val   Gly   Ala   Pro   Gly   Glu   Gly
      50                      55                      60

Asn   Ser   Thr   Gly   Ser   Leu   Tyr   Gln   Cys   Gln   Ser   Gly   Thr   Gly   His   Cys
65                      70                      75                            80

Leu   Pro   Val   Thr   Leu   Arg   Gly   Ser   Asn   Tyr   Thr   Ser   Lys   Tyr   Leu   Gly
                  85                      90                            95
```

```
Met Thr Leu Ala Thr Asp Pro Thr Asp Gly Ser Ile Leu Ala Cys Asp
            100             105                 110
Pro Gly Leu Ser Arg Thr Cys Asp Gln Asn Thr Tyr Leu Ser Gly Leu
        115             120                 125
Cys Tyr Leu Phe Arg Gln Asn Leu Gln Gly Pro Met Leu Gln Gly Arg
    130                 135                 140
Pro Gly Phe Gln Glu Cys Ile Lys Gly Asn Val Asp Leu Val Phe Leu
145                 150                 155                 160
Phe Asp Gly Ser Met Ser Leu Gln Pro Asp Glu Phe Gln Lys Ile Leu
                165             170                 175
Asp Phe Met Lys Asp Val Met Lys Lys Leu Ser Asn Thr Ser Tyr Gln
            180             185                 190
Phe Ala Ala Val Gln Phe Ser Thr Ser Tyr Lys Thr Glu Phe Asp Phe
        195             200                 205
Ser Asp Tyr Val Lys Trp Lys Asp Pro Asp Ala Leu Leu Lys His Val
    210                 215                 220
Lys His Met Leu Leu Leu Thr Asn Thr Phe Gly Ala Ile Asn Tyr Val
225                 230                 235                 240
Ala Thr Glu Val Phe Arg Glu Glu Leu Gly Ala Arg Pro Asp Ala Thr
                245             250                 255
Lys Val Leu Ile Ile Ile Thr Asp Gly Glu Ala Thr Asp Ser Gly Asn
            260             265                 270
Ile Asp Ala Ala Lys Asp Ile Ile Arg Tyr Ile Ile Gly Ile Gly Lys
        275             280                 285
His Phe Gln Thr Lys Glu Ser Gln Glu Thr Leu His Lys Phe Ala Ser
    290                 295                 300
Lys Pro Ala Ser Glu Phe Val Lys Ile Leu Asp Thr Phe Glu Lys Leu
305                 310                 315                 320
Lys Asp Leu Phe Thr Glu Leu Gln Lys Lys Ile Tyr Val Ile Glu Gly
                325             330                 335
Thr Ser Lys Gln Asp Leu Thr Ser Phe Asn Met Glu Leu Ser Ser Ser
            340             345                 350
Gly Ile Ser Ala Asp Leu Ser Arg Gly His Ala Val Val Gly Ala Val
        355             360                 365
Gly Ala Lys Asp Trp Ala Gly Gly Phe Leu Asp Leu Lys Ala Asp Leu
        370             375                 380
Gln Asp Asp Thr Phe Ile Gly Asn Glu Pro Leu Thr Pro Glu Val Arg
385                 390                 395                 400
Ala Gly Tyr Leu Gly Tyr Thr Val Thr Trp Leu Pro Ser Arg Gln Lys
                405             410                 415
Thr Ser Leu Leu Ala Ser Gly Ala Pro Arg Tyr Gln His Met Gly Arg
            420             425                 430
Val Leu Leu Phe Gln Glu Pro Gln Gly Gly Gly His Trp Ser Gln Val
        435             440                 445
Gln Thr Ile His Gly Thr Gln Ile Gly Ser Tyr Phe Gly Gly Glu Leu
    450                 455                 460
Cys Gly Val Asp Val Asp Gln Asp Gly Glu Thr Glu Leu Leu Leu Ile
465                 470                 475                 480
Gly Ala Pro Leu Phe Tyr Gly Glu Gln Arg Gly Gly Arg Val Phe Ile
                485             490                 495
Tyr Gln Arg Arg Gln Leu Gly Phe Glu Glu Val Ser Glu Leu Gln Gly
            500             505                 510
Asp Pro Gly Tyr Pro Leu Gly Arg Phe Gly Glu Ala Ile Thr Ala Leu
        515             520                 525
```

```
Thr  Asp  Ile  Asn  Gly  Asp  Gly  Leu  Val  Asp  Val  Ala  Val  Gly  Ala  Pro
     530                 535                 540

Leu  Glu  Glu  Gln  Gly  Ala  Val  Tyr  Ile  Phe  Asn  Gly  Arg  His  Gly  Gly
545                      550                 555                           560

Leu  Ser  Pro  Gln  Pro  Ser  Gln  Arg  Ile  Glu  Gly  Thr  Gln  Val  Leu  Ser
               565                      570                           575

Gly  Ile  Gln  Trp  Phe  Gly  Arg  Ser  Ile  His  Gly  Val  Lys  Asp  Leu  Glu
                580                      585                      590

Gly  Asp  Gly  Leu  Ala  Asp  Val  Ala  Val  Gly  Ala  Glu  Ser  Gln  Met  Ile
          595                      600                      605

Val  Leu  Ser  Ser  Arg  Pro  Val  Asp  Met  Val  Thr  Leu  Met  Ser  Phe
     610                 615                      620

Ser  Pro  Ala  Glu  Ile  Pro  Val  His  Glu  Val  Glu  Cys  Ser  Tyr  Ser  Thr
625                      630                      635                      640

Ser  Asn  Lys  Met  Lys  Glu  Gly  Val  Asn  Ile  Thr  Ile  Cys  Phe  Gln  Ile
                    645                      650                      655

Lys  Ser  Leu  Tyr  Pro  Gln  Phe  Gln  Gly  Arg  Leu  Val  Ala  Asn  Leu  Thr
               660                      665                      670

Tyr  Thr  Leu  Gln  Leu  Asp  Gly  His  Arg  Thr  Arg  Arg  Gly  Leu  Phe
          675                      680                      685

Pro  Gly  Gly  Arg  His  Glu  Leu  Arg  Arg  Asn  Ile  Ala  Val  Thr  Thr  Ser
     690                      695                      700

Met  Ser  Cys  Thr  Asp  Phe  Ser  Phe  His  Phe  Pro  Val  Cys  Val  Gln  Asp
705                      710                      715                      720

Leu  Ile  Ser  Pro  Ile  Asn  Val  Ser  Leu  Asn  Phe  Ser  Leu  Trp  Glu  Glu
                    725                      730                      735

Glu  Gly  Thr  Pro  Arg  Asp  Gln  Arg  Ala  Gln  Gly  Lys  Asp  Ile  Pro  Pro
               740                      745                      750

Ile  Leu  Arg  Pro  Ser  Leu  His  Ser  Glu  Thr  Trp  Glu  Ile  Pro  Phe  Glu
          755                      760                      765

Lys  Asn  Cys  Gly  Glu  Asp  Lys  Lys  Cys  Glu  Ala  Asn  Leu  Arg  Val  Ser
     770                      775                      780

Phe  Ser  Pro  Ala  Arg  Ser  Arg  Ala  Leu  Arg  Leu  Thr  Ala  Phe  Ala  Ser
785                      790                      795                      800

Leu  Ser  Val  Glu  Leu  Ser  Leu  Ser  Asn  Leu  Glu  Glu  Asp  Ala  Tyr  Trp
               805                      810                      815

Val  Gln  Leu  Asp  Leu  His  Phe  Pro  Pro  Gly  Leu  Ser  Phe  Arg  Lys  Val
          820                      825                      830

Glu  Met  Leu  Lys  Pro  His  Ser  Gln  Ile  Pro  Val  Ser  Cys  Glu  Glu  Leu
     835                      840                      845

Pro  Glu  Glu  Ser  Arg  Leu  Leu  Ser  Arg  Ala  Leu  Ser  Cys  Asn  Val  Ser
850                      855                      860

Ser  Pro  Ile  Phe  Lys  Ala  Gly  His  Ser  Val  Ala  Leu  Gln  Met  Met  Phe
865                      870                      875                      880

Asn  Thr  Leu  Val  Asn  Ser  Ser  Trp  Gly  Asp  Ser  Val  Glu  Leu  His  Ala
                    885                      890                      895

Asn  Val  Thr  Cys  Asn  Asn  Glu  Asp  Ser  Asp  Leu  Leu  Glu  Asp  Asn  Ser
               900                      905                      910

Ala  Thr  Thr  Ile  Ile  Pro  Ile  Leu  Tyr  Pro  Ile  Asn  Ile  Leu  Ile  Gln
          915                      920                      925

Asp  Gln  Glu  Asp  Ser  Thr  Leu  Tyr  Val  Ser  Phe  Thr  Pro  Lys  Gly  Pro
930                      935                      940

Lys  Ile  His  Gln  Val  Lys  His  Met  Tyr  Gln  Val  Arg  Ile  Gln  Pro  Ser
```

|     |     |     |     |     |     |     |     |     |     |     |     |     |     |     |     |
|---|---|---|---|---|---|---|---|---|---|---|---|---|---|---|---|
| 945 | | | | | 950 | | | | | 955 | | | | | 960 |
| Ile | His | Asp | His | Asn | Ile | Pro | Thr | Leu | Glu | Ala | Val | Val | Gly | Val | Pro |
| | | | | 965 | | | | | 970 | | | | | 975 | |
| Gln | Pro | Pro | Ser | Glu | Gly | Pro | Ile | Thr | His | Gln | Trp | Ser | Val | Gln | Met |
| | | | 980 | | | | | 985 | | | | | 990 | | |
| Glu | Pro | Pro | Val | Pro | Cys | His | Tyr | Glu | Asp | Leu | Glu | Arg | Leu | Pro | Asp |
| | | 995 | | | | | 1000 | | | | | 1005 | | | |
| Ala | Ala | Glu | Pro | Cys | Leu | Pro | Gly | Ala | Leu | Phe | Arg | Cys | Pro | Val | Val |
| | 1010 | | | | | 1015 | | | | | 1020 | | | | |
| Phe | Arg | Gln | Glu | Ile | Leu | Val | Gln | Val | Ile | Gly | Thr | Leu | Glu | Leu | Val |
| 1025 | | | | | 1030 | | | | | 1035 | | | | | 1040 |
| Gly | Glu | Ile | Glu | Ala | Ser | Ser | Met | Phe | Ser | Leu | Cys | Ser | Ser | Leu | Ser |
| | | | | 1045 | | | | | 1050 | | | | | 1055 | |
| Ile | Ser | Phe | Asn | Ser | Ser | Lys | His | Phe | His | Leu | Tyr | Gly | Ser | Asn | Ala |
| | | | | 1060 | | | | | 1065 | | | | | 1070 | |
| Ser | Leu | Ala | Gln | Val | Val | Met | Lys | Val | Asp | Val | Val | Tyr | Glu | Lys | Gln |
| | | | 1075 | | | | | 1080 | | | | | 1085 | | |
| Met | Leu | Tyr | Leu | Tyr | Val | Leu | Ser | Gly | Ile | Gly | Gly | Leu | Leu | Leu | Leu |
| | | | 1090 | | | | | 1095 | | | | | 1100 | | |
| Leu | Leu | Ile | Phe | Ile | Val | Leu | Tyr | Lys | Val | Gly | Phe | Phe | Lys | Arg | Asn |
| 1105 | | | | | 1110 | | | | | 1115 | | | | | 1120 |
| Leu | Lys | Glu | Lys | Met | Glu | Ala | Gly | Arg | Gly | Val | Pro | Asn | Gly | Ile | Pro |
| | | | | 1125 | | | | | 1130 | | | | | 1135 | |
| Ala | Glu | Asp | Ser | Glu | Gln | Leu | Ala | Ser | Gly | Gln | Glu | Ala | Gly | Asp | Pro |
| | | | | 1140 | | | | | 1145 | | | | | 1150 | |
| Gly | Cys | Leu | Lys | Pro | Leu | His | Glu | Lys | Asp | Ser | Glu | Ser | Gly | Gly | Gly |
| | | | 1155 | | | | | 1160 | | | | | 1165 | | |
| Lys | Asp | | | | | | | | | | | | | | |
| 1170 | | | | | | | | | | | | | | | |

( 2 ) INFORMATION FOR SEQ ID NO:3:

( i ) SEQUENCE CHARACTERISTICS:
        ( A ) LENGTH: 531 amino acids
        ( B ) TYPE: amino acid
        ( D ) TOPOLOGY: both ( i i ) MOLECULE TYPE: protein ( v i ) ORIGINAL SOURCE:
        ( A ) ORGANISM: Homo sapiens
        ( G ) CELL TYPE: T-cell
        ( H ) CELL LINE: HL-60

( i x ) FEATURE:
        ( A ) NAME/KEY: Region
        ( B ) LOCATION: 1..25
        ( D ) OTHER INFORMATION: /label=Signal
            / note= "Signal sequence"

( i x ) FEATURE:
        ( A ) NAME/KEY: Region
        ( B ) LOCATION: 41..100
        ( D ) OTHER INFORMATION: /label=Ig1

( i x ) FEATURE:
        ( A ) NAME/KEY: Region
        ( B ) LOCATION: 128..190
        ( D ) OTHER INFORMATION: /label=Ig2

( i x ) FEATURE:
        ( A ) NAME/KEY: Region
        ( B ) LOCATION: 230..294
        ( D ) OTHER INFORMATION: /label=Ig3

(  i x  ) FEATURE:
            ( A ) NAME/KEY: Region
            ( B ) LOCATION: 325..375
            ( D ) OTHER INFORMATION: /label=Ig4

(  i x  ) FEATURE:
            ( A ) NAME/KEY: Region
            ( B ) LOCATION: 413..461
            ( D ) OTHER INFORMATION: /label=Ig5

(  i x  ) FEATURE:
            ( A ) NAME/KEY: Duplication
            ( B ) LOCATION: 481..503
            ( D ) OTHER INFORMATION: /label=Trans
                    / note= "Transmembrane domain"

(  i x  ) FEATURE:
            ( A ) NAME/KEY: Binding-site
            ( B ) LOCATION: 152..154
            ( D ) OTHER INFORMATION: /label=Attachment
                    / note= "Cell attachment site"

( x ) PUBLICATION INFORMATION:
            ( A ) AUTHORS: Pigott,
                    Power,
            ( B ) TITLE: ICAM-1 Amino acid sequence (from HL-60)
            ( C ) JOURNAL: The Adhesion Molecule Facts Book
            ( F ) PAGES: 75-75
            ( G ) DATE: 1993
            ( K ) RELEVANT RESIDUES IN SEQ ID NO:3: FROM 1 TO 531

( x i ) SEQUENCE DESCRIPTION: SEQ ID NO:3:

| Met | Ala | Pro | Ser | Ser | Pro | Arg | Pro | Ala | Leu | Pro | Ala | Leu | Leu | Val | Leu |
|---|---|---|---|---|---|---|---|---|---|---|---|---|---|---|---|
| 1 | | | | 5 | | | | | 10 | | | | | 15 | |
| Leu | Gly | Ala | Leu | Phe | Pro | Gly | Pro | Gly | Asn | Ala | Gln | Thr | Ser | Val | Ser |
| | | | 20 | | | | 25 | | | | | 30 | | | |
| Pro | Ser | Lys | Val | Ile | Leu | Pro | Arg | Gly | Gly | Ser | Val | Leu | Val | Thr | Cys |
| | | 35 | | | | | 40 | | | | | 45 | | | |
| Ser | Thr | Ser | Cys | Asp | Gln | Pro | Lys | Leu | Leu | Gly | Ile | Glu | Thr | Pro | Leu |
| | 50 | | | | | 55 | | | | | 60 | | | | |
| Pro | Lys | Lys | Glu | Leu | Leu | Leu | Pro | Gly | Asn | Asn | Arg | Lys | Val | Tyr | Glu |
| 65 | | | | | 70 | | | | | 75 | | | | | 80 |
| Leu | Ser | Asn | Val | Gln | Glu | Asp | Ser | Gln | Pro | Met | Cys | Tyr | Ser | Asn | Cys |
| | | | | 85 | | | | | 90 | | | | | 95 | |
| Pro | Asp | Gly | Ser | Thr | Ala | Lys | Thr | Phe | Leu | Thr | Val | Tyr | Trp | Thr | Pro |
| | | | 100 | | | | | 105 | | | | | 110 | | |
| Glu | Arg | Val | Glu | Leu | Ala | Pro | Leu | Pro | Ser | Trp | Gln | Pro | Val | Gly | Lys |
| | | 115 | | | | | 120 | | | | | 125 | | | |
| Asn | Leu | Thr | Leu | Arg | Cys | Gln | Val | Glu | Gly | Gly | Ala | Pro | Arg | Ala | Asn |
| | 130 | | | | | 135 | | | | | 140 | | | | |
| Leu | Thr | Val | Val | Leu | Leu | Arg | Gly | Glu | Lys | Glu | Leu | Lys | Arg | Glu | Pro |
| 145 | | | | | 150 | | | | | 155 | | | | | 160 |
| Ala | Val | Gly | Glu | Pro | Ala | Glu | Val | Thr | Thr | Thr | Val | Leu | Val | Arg | Arg |
| | | | | 165 | | | | | 170 | | | | | 175 | |
| Asp | His | His | Gly | Ala | Asn | Phe | Ser | Cys | Arg | Thr | Glu | Leu | Asp | Leu | Arg |
| | | | 180 | | | | | 185 | | | | | 190 | | |
| Pro | Gln | Gly | Leu | Glu | Leu | Phe | Glu | Asn | Thr | Ser | Ala | Pro | Tyr | Gln | Leu |
| | | | 195 | | | | 200 | | | | | 205 | | | |
| Gln | Thr | Phe | Val | Leu | Pro | Ala | Thr | Pro | Pro | Gln | Leu | Val | Ser | Pro | Arg |
| | 210 | | | | | 215 | | | | | 220 | | | | |
| Val | Leu | Glu | Val | Asp | Thr | Gln | Gly | Thr | Val | Val | Cys | Ser | Leu | Asp | Gly |
| 225 | | | | | 230 | | | | | 235 | | | | | 240 |
| Leu | Phe | Pro | Val | Ser | Glu | Ala | Gln | Val | His | Leu | Ala | Leu | Gly | Asp | Gln |
| | | | | 245 | | | | | 250 | | | | | 255 | |

| | | | | | | | | | | | | | | |
|---|---|---|---|---|---|---|---|---|---|---|---|---|---|---|
|Arg|Leu|Asn|Pro<br>260|Thr|Val|Thr|Tyr|Gly<br>265|Asn|Asp|Ser|Phe|Ser<br>270|Ala|Lys|
|Ala|Ser|Val<br>275|Ser|Val|Thr|Ala|Glu<br>280|Asp|Glu|Gly|Thr|Gln<br>285|Arg|Leu|Thr|
|Cys|Ala<br>290|Val|Ile|Ile|Gly|Asn<br>295|Gln|Ser|Gln|Glu|Thr<br>300|Leu|Gln|Thr|Val|
|Thr<br>305|Ile|Tyr|Ser|Phe|Pro<br>310|Ala|Pro|Asn|Val|Ile<br>315|Leu|Thr|Lys|Pro|Glu<br>320|
|Val|Ser|Glu|Gly|Thr<br>325|Glu|Val|Thr|Val|Lys<br>330|Cys|Glu|Ala|His|Pro<br>335|Arg|
|Ala|Lys|Val|Thr<br>340|Leu|Asn|Gly|Val|Pro<br>345|Ala|Gln|Pro|Leu|Gly<br>350|Pro|Arg|
|Ala|Gln|Leu|Leu<br>355|Leu|Lys|Ala|Thr<br>360|Pro|Glu|Asp|Asn|Gly<br>365|Arg|Ser|Phe|
|Ser|Cys<br>370|Ser|Ala|Thr|Leu|Glu<br>375|Val|Ala|Gly|Gln|Leu<br>380|Ile|His|Lys|Asn|
|Gln<br>385|Thr|Arg|Glu|Leu|Arg<br>390|Val|Leu|Tyr|Gly|Pro<br>395|Arg|Leu|Asp|Glu|Arg<br>400|
|Asp|Cys|Pro|Gly|Asn<br>405|Trp|Thr|Trp|Pro|Glu<br>410|Asn|Ser|Gln|Gln|Thr<br>415|Pro|
|Met|Cys|Gln|Ala<br>420|Trp|Gly|Asn|Pro|Leu<br>425|Pro|Glu|Leu|Lys|Cys<br>430|Leu|Lys|
|Asp|Gly|Thr<br>435|Phe|Pro|Leu|Pro|Ile<br>440|Gly|Glu|Ser|Val|Thr<br>445|Val|Thr|Arg|
|Asp|Leu|Glu<br>450|Gly|Thr|Tyr|Leu<br>455|Cys|Arg|Ala|Arg|Ser<br>460|Thr|Gln|Gly|Glu|
|Val|Thr|Arg|Glu|Val<br>465| |Thr|Val<br>470|Asn|Val|Leu|Ser<br>475|Pro|Arg|Tyr|Glu|Ile<br>480|
|Val|Ile|Ile|Thr|Val<br>485|Val|Ala|Ala|Val<br>490|Ile|Met|Gly|Thr|Ala<br>495|Gly|
|Leu|Ser|Thr|Tyr<br>500|Leu|Tyr|Asn|Arg|Gln<br>505|Arg|Lys|Ile|Lys|Lys<br>510|Tyr|Arg|
|Leu|Gln|Gln<br>515|Ala|Gln|Lys|Gly|Thr<br>520|Pro|Met|Lys|Pro|Asn<br>525|Thr|Gln|Ala|
|Thr|Pro|Pro<br>530| | | | | | | | | | | | | |

( 2 ) INFORMATION FOR SEQ ID NO:4:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Homo sapiens
        ( G ) CELL TYPE: T-cell
        ( H ) CELL LINE: HL-60

( x i ) SEQUENCE DESCRIPTION: SEQ ID NO:4:

| | | | | | | | | | | | | | | |
|---|---|---|---|---|---|---|---|---|---|---|---|---|---|---|
|Gln<br>1|Thr|Ser|Val|Ser<br>5|Pro|Ser|Lys|Val|Ile<br>10|Leu|Pro|Arg|Gly|Gly<br>15|Ser|
|Val|Leu|Val|Thr|Gly| | | | | | | | | | |

20

(2) INFORMATION FOR SEQ ID NO:5:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Homo sapiens
        (G) CELL TYPE: T-cell
        (H) CELL LINE: HL-60

(xi) SEQUENCE DESCRIPTION: SEQ ID NO:5:

```
Xaa  Gln  Thr  Ser  Val  Ser  Pro  Ser  Lys  Val  Ile  Leu  Pro  Arg  Gly  Gly
1                   5                        10                       15
Ser  Val  Leu  Val  Thr  Gly
                20
```

(2) INFORMATION FOR SEQ ID NO:6:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Homo sapiens
        (G) CELL TYPE: T-cell
        (H) CELL LINE: HL-60

(xi) SEQUENCE DESCRIPTION: SEQ ID NO:6:

```
Gln  Thr  Ser  Val  Ser  Pro  Ser  Lys  Val  Ile  Leu  Pro  Arg  Gly  Gly  Ser
1                   5                        10                       15
Val  Leu  Val  Thr  Gly
                20
```

(2) INFORMATION FOR SEQ ID NO:7:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Homo sapiens
        (G) CELL TYPE: T-cell
        (H) CELL LINE: HL-60

(xi) SEQUENCE DESCRIPTION: SEQ ID NO:7:

```
Cys  Leu  Pro  Arg  Gly  Gly  Ser  Val  Leu  Val  Thr  Cys
1                   5                        10
```

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( D ) TOPOLOGY: cyclic ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Homo sapiens
        ( G ) CELL TYPE: T-cell
        ( H ) CELL LINE: HL-60

( x i ) SEQUENCE DESCRIPTION: SEQ ID NO:8:

Cys Leu Pro Arg Gly Gly Ser Val Leu Val Thr Cys
    1                5                      10

( 2 ) INFORMATION FOR SEQ ID NO:9:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Homo sapiens
        ( G ) CELL TYPE: T-cell
        ( H ) CELL LINE: HL-60

( x i ) SEQUENCE DESCRIPTION: SEQ ID NO:9:

Leu Pro Arg Gly Gly Ser Val Leu Val Thr Gly
    1              5                      10

( 2 ) INFORMATION FOR SEQ ID NO:10:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Homo sapiens
        ( G ) CELL TYPE: T-cell
        ( H ) CELL LINE: HL-60

( x i ) SEQUENCE DESCRIPTION: SEQ ID NO:10:

Gln Thr Ser Val Ser Pro Ser Lys Val Ile
    1              5                      10

( 2 ) INFORMATION FOR SEQ ID NO:11:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
    ( A ) ORGANISM: Homo sapiens
    ( G ) CELL TYPE: T-cell
    ( H ) CELL LINE: HL-60

( x i ) SEQUENCE DESCRIPTION: SEQ ID NO:11:

```
Asp Gln Pro Lys Leu Leu Gly Ile Glu Thr Pro Leu Pro Lys Lys Glu
1               5                   10                  15
Leu Leu Leu Pro Gly Asn Asn Arg Lys
                20              25
```

( 2 ) INFORMATION FOR SEQ ID NO:12:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Homo sapiens
        ( F ) TISSUE TYPE: tonsil ( x i ) SEQUENCE DESCRIPTION: SEQ ID NO:12:

```
Lys Glu Leu Leu Leu Pro Gly Asn Asn Arg Lys Val Tyr Glu Leu Ser
1               5                   10                  15
Asn Val Gln Glu Asp Ser Gln Pro
                20
```

( 2 ) INFORMATION FOR SEQ ID NO:13:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Homo sapiens
        ( G ) CELL TYPE: T-cell
        ( H ) CELL LINE: HL-60

( x i ) SEQUENCE DESCRIPTION: SEQ ID NO:13:

```
Pro Ser Lys Val Ile Leu Pro Arg Gly Gly
1               5                   10
```

( 2 ) INFORMATION FOR SEQ ID NO:14:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
    ( A ) ORGANISM: Homo sapiens
    ( G ) CELL TYPE: T-cell
    ( H ) CELL LINE: HL-60

( x i ) SEQUENCE DESCRIPTION: SEQ ID NO:14:

```
Xaa  Pro  Ser  Lys  Val  Ile  Leu  Pro  Arg  Gly  Gly  Cys
1                   5                        10
```

( 2 ) INFORMATION FOR SEQ ID NO:15:

( i ) SEQUENCE CHARACTERISTICS:
        ( A ) LENGTH: 12 amino acids
        ( B ) TYPE: amino acid
        ( D ) TOPOLOGY: cyclic ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Homo sapiens
        ( G ) CELL TYPE: T-cell
        ( H ) CELL LINE: HL-60

( x i ) SEQUENCE DESCRIPTION: SEQ ID NO:15:

```
Xaa  Pro  Ser  Lys  Val  Ile  Leu  Pro  Arg  Gly  Gly  Cys
1                   5                        10
```

( 2 ) INFORMATION FOR SEQ ID NO:16:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Homo sapiens
        ( F ) TISSUE TYPE: tonsil ( x i ) SEQUENCE DESCRIPTION: SEQ ID NO:16:

```
Asp  Leu  Ser  Tyr  Ser  Leu  Asp  Asp  Leu  Arg  Asn  Val  Lys  Lys  Leu  Gly
1                   5                        10                       15
Gly  Asp  Leu  Leu  Arg  Ala  Leu  Asn  Glu
                20                        25
```

( 2 ) INFORMATION FOR SEQ ID NO:17:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Homo sapiens
        ( G ) CELL TYPE: T-cell ( H ) CELL LINE: HL-60

( x i ) SEQUENCE DESCRIPTION: SEQ ID NO:17:

Gly Val Asp Val Asp Gln Asp Gly Glu Thr Glu Leu Ile Gly Ala Pro
        1               5                   10                  15

Leu Phe Tyr Gly Glu Gln Arg Gly
                        20

( 2 ) INFORMATION FOR SEQ ID NO:18:

( i ) SEQUENCE CHARACTERISTICS:
            ( A ) LENGTH: 24 amino acids
            ( B ) TYPE: amino acid
            ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
            ( A ) ORGANISM: Homo sapiens
            ( G ) CELL TYPE: T-cell
            ( H ) CELL LINE: HL-60

( x i ) SEQUENCE DESCRIPTION: SEQ ID NO:18:

Ile Thr Asp Gly Glu Ala Thr Asp Ser Gly Asn Ile Asp Ala Ala Lys
        1               5                   10                  15

Asp Ile Ile Tyr Ile Ile Gly Ile
                        20

( 2 ) INFORMATION FOR SEQ ID NO:19:

( i ) SEQUENCE CHARACTERISTICS:
            ( A ) LENGTH: 24 amino acids
            ( B ) TYPE: amino acid
            ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
            ( A ) ORGANISM: Homo sapiens
            ( G ) CELL TYPE: T-cell
            ( H ) CELL LINE: HL-60

( x i ) SEQUENCE DESCRIPTION: SEQ ID NO:19:

Ile Thr Asp Gly Glu Ala Thr Asp Ser Gly Asn Ile Asp Ala Ala Lys
        1               5                   10                  15

Asp Ile Ile Tyr Ile Ile Gly Ile
                        20